United States Patent
Foldvari

(10) Patent No.: US 11,801,221 B2
(45) Date of Patent: Oct. 31, 2023

(54) LIPID VESICLE COMPOSITIONS WITH PENETRATION ENHANCING AGENTS

(71) Applicant: DDS RESEARCH INC., Kitchener (CA)

(72) Inventor: Marianna Foldvari, Kitchener (CA)

(73) Assignee: DDS RESEARCH INC., Kitchener (CA)

( * ) Notice: Subject to any disclaimer, the term of this patent is extended or adjusted under 35 U.S.C. 154(b) by 0 days.

(21) Appl. No.: 17/841,924

(22) Filed: Jun. 16, 2022

(65) Prior Publication Data

US 2022/0313606 A1    Oct. 6, 2022

Related U.S. Application Data

(63) Continuation of application No. 17/702,608, filed on Mar. 23, 2022, which is a continuation of application No. PCT/CA2020/051275, filed on Sep. 23, 2020.

(Continued)

(51) Int. Cl.
*A61K 9/127* (2006.01)
*A61P 17/00* (2006.01)
(Continued)

(52) U.S. Cl.
CPC ............... *A61K 9/127* (2013.01); *A61K 8/14* (2013.01); *A61K 9/0014* (2013.01);
(Continued)

(58) Field of Classification Search
CPC ........ A61K 9/127; A61K 8/14; A61K 9/0014; A61K 9/1273; A61K 47/10; A61K 47/14;
(Continued)

(56) References Cited

U.S. PATENT DOCUMENTS 4,372,977 A * 2/1983 Lover ................. A01N 31/02
514/723
4,968,450 A * 11/1990 Kamegai ............. C11D 1/722
510/480

(Continued)

FOREIGN PATENT DOCUMENTS

CA    2324403 A1    7/2000
CA    2458443 A1    3/2003

(Continued)

OTHER PUBLICATIONS

Dhamecha: Drug Vehicle Based Approaches of Penetration Enhancement. 1(1):24-46 (2009).

(Continued)

*Primary Examiner* — Gollamudi S Kishore
(74) *Attorney, Agent, or Firm* — Wilson Sonsini Goodrich & Rosati

(57) ABSTRACT

The present application is related to a pharmaceutical composition a biphasic lipid vesicle comprising a lipid bilayer comprising vesicle forming lipids; an oil-in-water emulsion stabilized by one or more surfactants; one or more compounds; and one or more penetration enhancing agents. The one or more penetration enhancing agents include one or more non-ionic surfactants having a hydrophilic-lipophilic balance (HLB) of about 10 or less, alone or combination with one or more penetration enhancing agents selected from one or more of terpenes, alkaloids, salicylate derivatives, and polycationic surfactants and combinations thereof. The present application is also related to a pharmaceutical composition comprising a biphasic lipid vesicle comprising a lipid bilayer comprising vesicle forming lipids; an oil-in-water emulsion stabilized by one or more polycationic surfactants; and one or more compounds.

16 Claims, 4 Drawing Sheets

Related U.S. Application Data

(60) Provisional application No. 62/904,606, filed on Sep. 23, 2019, provisional application No. 62/904,584, filed on Sep. 23, 2019.

(51) Int. Cl.
| | |
|---|---|
| *A61K 8/14* | (2006.01) |
| *A61K 9/00* | (2006.01) |
| *A61K 47/10* | (2017.01) |
| *A61K 47/14* | (2017.01) |
| *A61K 47/18* | (2017.01) |
| *A61K 47/22* | (2006.01) |
| *A61K 47/24* | (2006.01) |
| *A61Q 19/08* | (2006.01) |

(52) U.S. Cl.
CPC ............ *A61K 9/1273* (2013.01); *A61K 47/10* (2013.01); *A61K 47/14* (2013.01); *A61K 47/186* (2013.01); *A61K 47/22* (2013.01); *A61K 47/24* (2013.01); *A61P 17/00* (2018.01); *A61Q 19/08* (2013.01)

(58) Field of Classification Search
CPC ...... A61K 47/186; A61K 47/22; A61K 47/24; A61K 47/08; A61K 47/26; A61K 9/1075; A61K 47/28; A61K 47/44; A61K 8/0212; A61K 8/44; A61K 8/86; A61P 17/00; A61Q 19/08
See application file for complete search history.

(56) References Cited

U.S. PATENT DOCUMENTS

| | | | | |
|---|---|---|---|---|
| 5,804,216 | A | | 9/1998 | Terren et al. |
| 5,853,755 | A | | 12/1998 | Foldvari |
| 5,993,852 | A | * | 11/1999 | Foldvari ............... A61K 9/127 264/43 |
| 6,656,499 | B1 | * | 12/2003 | Foldvari ............. A61K 9/7023 424/450 |
| 6,696,424 | B1 | * | 2/2004 | Wheeler ............... C12N 15/88 564/160 |
| 11,130,782 | B2 | | 9/2021 | Love |
| 2004/0219232 | A1 | | 11/2004 | Lipton |
| 2006/0040354 | A1 | | 2/2006 | O'Keefe |
| 2006/0233901 | A1 | * | 10/2006 | Jamieson ............... A61P 25/00 424/760 |
| 2008/0008747 | A1 | | 1/2008 | Royds |
| 2009/0081142 | A1 | * | 3/2009 | Omura .................... A61K 8/342 424/59 |
| 2009/0098171 | A1 | | 4/2009 | Alard et al. |
| 2010/0112016 | A1 | | 5/2010 | Carli et al. |
| 2010/0166689 | A1 | | 7/2010 | Waugh |
| 2010/0278845 | A1 | | 11/2010 | Heavner |
| 2012/0093718 | A1 | | 4/2012 | Parchment et al. |
| 2012/0196796 | A1 | | 8/2012 | Soares et al. |
| 2016/0151283 | A1 | | 6/2016 | Manca et al. |
| 2017/0105936 | A1 | | 4/2017 | Cerundolo et al. |
| 2017/0304232 | A1 | | 10/2017 | Khan et al. |
| 2017/0313756 | A1 | | 11/2017 | Perricone et al. |
| 2018/0177739 | A1 | * | 6/2018 | Johnson ............... A61K 9/146 |
| 2018/0360757 | A1 | | 12/2018 | Doroudian et al. |
| 2019/0183787 | A1 | * | 6/2019 | Dizerega ............... A61P 35/00 |
| 2019/0209498 | A1 | * | 7/2019 | Khan ...................... A61K 9/06 |
| 2020/0062804 | A1 | | 2/2020 | Tanaka et al. |
| 2020/0407768 | A1 | | 12/2020 | Hirota et al. |
| 2022/0048950 | A1 | | 2/2022 | Love |
| 2022/0218611 | A1 | | 7/2022 | Foldvari |
| 2023/0143474 | A1 | | 5/2023 | Foldvari |
| 2023/0157954 | A1 | | 5/2023 | Foldvari |
| 2023/0270635 | A1 | | 8/2023 | Love et al. |

FOREIGN PATENT DOCUMENTS

| | | | |
|---|---|---|---|
| CN | 108778244 | A | 11/2018 |
| EP | 2498792 | A1 | 9/2012 |
| FR | 2846238 | A1 | 4/2004 |
| FR | 2876577 | A1 | 4/2006 |
| KR | 100748035 | B1 | 8/2007 |
| WO | WO-9911247 | A1 | 3/1999 |
| WO | WO-0135998 | A1 | 5/2001 |
| WO | WO-2006012414 | A2 | 2/2006 |
| WO | WO-2008119160 | A1 | 10/2008 |
| WO | WO-2011060083 | A1 | 5/2011 |
| WO | WO-2015023601 | A1 | 2/2015 |
| WO | WO-2018144093 | A2 | 8/2018 |
| WO | WO-2020081583 | A1 | 4/2020 |
| WO | WO-2021056106 | A1 | 4/2021 |
| WO | WO-2021216572 | A1 | 10/2021 |
| WO | WO-2022204287 | A1 | 9/2022 |
| WO | WO-2022204305 | A2 | 9/2022 |
| WO | WO-2022204308 | A1 | 9/2022 |
| WO | WO-2022204309 | A1 | 9/2022 |
| WO | WO-2023081259 | A2 | 5/2023 |

OTHER PUBLICATIONS

Gupta et al.: Biocompatible Micro emulsions and Their Prospective Uses in Drug Deliver. Journal of Pharmaceutical Sciences. 97(1):22-45. (2008).
Otto et al.: Formulation effects of topical emulsions on transdermal and dermal delivery. International Journal of Cosmetic Science. 31:1-19 (2009).
Paliwal et al.: Pharmaceutical Considerations of Microemulsion as a Drug Delivery System. Journal of Drug Delivery & Therapeutics. 9(4-s):661-665 (2019).
Talegoankar et al.: Microemulsions: A Novel Approach to Enhanced Drug Delivery. Recent Patents on Drug Delivery & Formulation. 2:238-257 (2008).
Van Staden: Development of topical-transdermal self-emulsifying drug delivery systems. Sci. Pharm. 88:17 (2020).
Zhou et al.: Nano-formulations for transdermal drug delivery: A review. Chinese Chemical Letters. 29:1713-1724 (2018).
Kirby et al.: Gemini surfactants: new synthetic vectors for gene transfection. Angew Chem Int Ed Engl. 42(13):1448-1457 (2003).
Lane. Skin penetration enhancers. Int. J. Pharm. 447(1-2):12-21 (2013).
Lotioncrafter. Lotioncrafter.com. Sorbitan Stearate Product Info. Sep. 20, 2020 [retrieved May 18, 2022] https://webarchive.org/web/20200920113912/https://lotionlcrafter.com/products/sorbitan-stearate [entire document].
Menger et al.: Gemini Surfactants. Angew Chem Int Ed Engl. 39(11):1906-1920 (2000).
PCT/CA2020/051275 International Search Report and Written Opinion dated Dec. 21, 2020.
PCT/US2022/021554 International Search Report and Written Opinion dated Jun. 10, 2022.
PCT/US2022/021579 Invitation to Pay Additional Fees dated Jul. 22, 2022.
PCT/US2022/021585 International Search Report and Written Opinion dated Jul. 7, 2022.
Williams et al.: Penetration Enhancers. Advanced Drug Delivery Reviews. 64:128-137 (2012).
Zasada et al.: The assessment of the effect of a cosmetic product brightening the skin of people with discolorations of different etiology. Journal of Cosmetic Dermatology. 15:493-502 (2016).
Co-pending U.S. Application No. 202318150144, inventor Foldvari; Marianna, filed on Jan. 4, 2023.
Co-pending U.S. Application No. 202318150145, inventor Foldvari; Marianna, filed on Jan. 4, 2023.
Lichtenberg et al.: The Mechanism of Detergent Solubilization of Lipid Bilayers. Biophysical Journal. 105:289-299 (2013).
McClements: Nanoemulsions versus microemulsions: terminology, differences, and similarities. Soft Matter. 8:1719-1729 (2012).
PCT/US2022/021579 International Search Report and Written Opinion dated Oct. 5, 2022.

(56) References Cited

OTHER PUBLICATIONS

Chinese Patent Application No. 2020800813833 First Office Action dated Apr. 27, 2023.
Falla et al.: Cosmeceuticals and peptides. Clinics in Dermatology 27:485-494 (2009).
Folvari: Observations of membrane fusion in a liposome dispersion: the missing fusion intermediate? F1000 Research. 4(4):1-11 (2015).
Koivukangas et al.: Increased collagen synthesis in psoriasis in vivo. Arch Dermatol Res. 287:171-175 (1995).
PCT/US2022/048780 International Search Report and Written Opinion dated Apr. 27, 2023.
Shen et al.: Effect of Nonionic Surfactants on Percutaneous Absorption of Salicylic Acid and Sodium Salicylate in the Presence of Dimethyl Sulfoxide. Journal of Pharmaceutical Sciences. 65(12):1780-1783 (1976).
Shin et al.: Effects of non-ionic surfactants as permeation enhancers towards piroxicam from the poloxamer gel through rat skins. International Journal of Pharmaceutics. 222(2):199-203 (2001).
Shin et al.: Enhanced transdermal delivery of triprolidine from the ethylene-vinyl acetate matrix. European Journal of Pharmaceutics and Biopharmaceutics. 54(3):325-328 (2002).
Som, Iti et al. Status of surfactants as penetration enhancers in transdermal drug delivery. Journal of pharmacy & bioallied sciences vol. 4,1 (2012): 2-9.
Spicer et al. Selective chemical protein modification. Nature Communications 5:4740 (2014).
U.S. Appl. No. 18/150,144 Office Action dated Apr. 18, 2023.
U.S. Appl. No. 18/150,145 Office Action dated May 19, 2023.
U.S. Appl. No. 18/150,145 Office Action dated May 8, 2023.

\* cited by examiner

LIPID VESICLE COMPOSITIONS WITH PENETRATION ENHANCING AGENTS

RELATED APPLICATIONS

The present application claims the benefit of priority of U.S. provisional patent application No. 62/904,606 filed on Sep. 23, 2019, and U.S. provisional patent application No. 62/904,584 filed on Sep. 23, 2019, the contents of both of which are incorporated herein by reference in their entirety.

FIELD

The present technology generally relates to lipid vesicle formulations for the topical delivery of a therapeutic compound where the lipid vesicle formulation comprises one or more penetration enhancing agents such as one or more surfactants having an HLB of 10 or less.

BACKGROUND

The barrier properties of the skin prevent most external substances to permeate into the body. The properties of most drugs fall outside the optimum range of permeability and hence require some type of an enhancer to be therapeutically useful. The main barrier controlling dermal protein delivery is the outermost layer of the skin, the stratum corneum (SC). In mammalian skin, the SC (10 to 20 µm thick) consists of dead corneocytes that are composed of cross-linked keratin and intercellular lipids organized in bilayers. Underneath the SC is the viable epidermis (50 to 100 µm) and deeper is the dermis (1-2 mm) that contains a rich capillary bed for drug absorption just below the dermal-epidermal junction. The generally accepted size limit of molecules for passive delivery through the skin is below 500 Da. Unassisted penetration of molecules above this molecular weight through intact skin is extremely low.

Different delivery approaches have been developed to facilitate the diffusion of drugs into or through the skin. The enhanced permeation through the skin could be achieved by physical methods (e.g. microneedles, thermal ablation), electrical methods (e.g. electroporation, iontophoresis) or chemical methods (e.g. chemical enhancers). Although the use of physical and electrical methods to enhance the drug permeation through the skin has shown some success in enhancing the delivery of both small and large molecules, there are still significant hurdles to overcome before approval. Several non-invasive delivery vehicles, mostly lipid-based, have been developed for protein delivery, such as, liposomes, transfersomes, niosomes and solid lipid nanoparticles. However, these delivery systems were only able to deliver limited amount of proteins into the different skin layers, as compared to the other invasive techniques.

U.S. Pat. Nos. 5,853,755 and 5,993,851 describe biphasic lipid vesicle compositions and methods of their preparation. U.S. Pat. No. 5,993,852 describes biphasic lipid vesicle compositions for transdermal administration of an immunogen.

SUMMARY

The present disclosure includes a biphasic lipid vesicle composition comprising:
a) lipid vesicles each comprising a lipid bilayer comprising vesicle forming lipids,
b) an oil-in-water emulsion entrapped in the biphasic lipid vesicles, and stabilized by one or more surfactants;
c) one or more compounds entrapped in the lipid bilayer and/or the oil-in-water emulsion;
d) one or more penetration enhancing agents entrapped in the lipid bilayer and/or the oil-in-water emulsion;
wherein the one or more penetration enhancing agents are one or more non-ionic surfactants having a hydrophilic-lipophilic balance (HLB) of about 10 or less.

The present application also includes a biphasic lipid vesicle composition comprising:
a) lipid vesicles comprising a lipid bilayer comprising vesicle forming lipids,
b) an oil-in-water emulsion entrapped in the biphasic lipid vesicles, and comprising one or more polycationic surfactants; and
c) one or more compounds entrapped in the lipid bilayer and/or the oil-in-water emulsion.

The present application also further includes method of preparing biphasic lipid vesicles of the disclosure comprising:
a) preparing an oil-in-water emulsion comprising one or more surfactants, by mixing oil components of the oil-in-water emulsion with aqueous components of the oil-in-water emulsion, wherein the oil components and/or the aqueous components of the oil-in-water emulsion comprises the one or more surfactants;
b) solubilizing vesicle forming lipids in an acceptable solvent other than water;
c) adding one or more compounds and one or more penetration enhancing agents to the oil components and/or the aqueous components of step a), and/or the solubilized vesicle forming lipids of step b);
d) adding the oil-in-water emulsion to the solubilized vesicle forming lipids; and
e) mixing the oil-in-water emulsion and the solubilized vesicle forming lipids under mixing conditions effective to form the biphasic lipid vesicles comprising a lipid bilayer comprising vesicle forming lipids, and an oil-in-water emulsion entrapped in the biphasic lipid vesicles.

The present application also further includes a method of delivering one or more compounds by administering biphasic lipid vesicle compositions of the disclosure topically to the skin or mucosal membrane to a subject.

The present application also includes a method of improving topical delivery of one or more compounds comprising administering an effective amount of biphasic lipid vesicle compositions of the disclosure to the skin or mucosal membrane of a subject in need thereof.

The present application also further includes a method of treating or preventing skin conditions related to excessive or defective collagen production in a subject comprising administering to the subject in need thereof, an effective amount of lipid vesicle cosmetic compositions of the disclosure to a subject in need thereof.

The present application also further includes method of treating disease, disorder or condition treatable by delivering one or more therapeutic compounds by administering a therapeutically effective amount of biphasic lipid vesicle pharmaceutical compositions of the disclosure topically to the skin or mucosal membrane to a subject in need thereof.

Other features and advantages of the present application will become apparent from the following detailed description. It should be understood, however, that the detailed description and the specific examples, while indicating embodiments of the disclosure, are given by way of illustration only and the scope of the claims should not be limited by these embodiments, but should be given the broadest interpretation consistent with the description as a whole.

DETAILED DESCRIPTION

I. Definitions

Figure 1A:
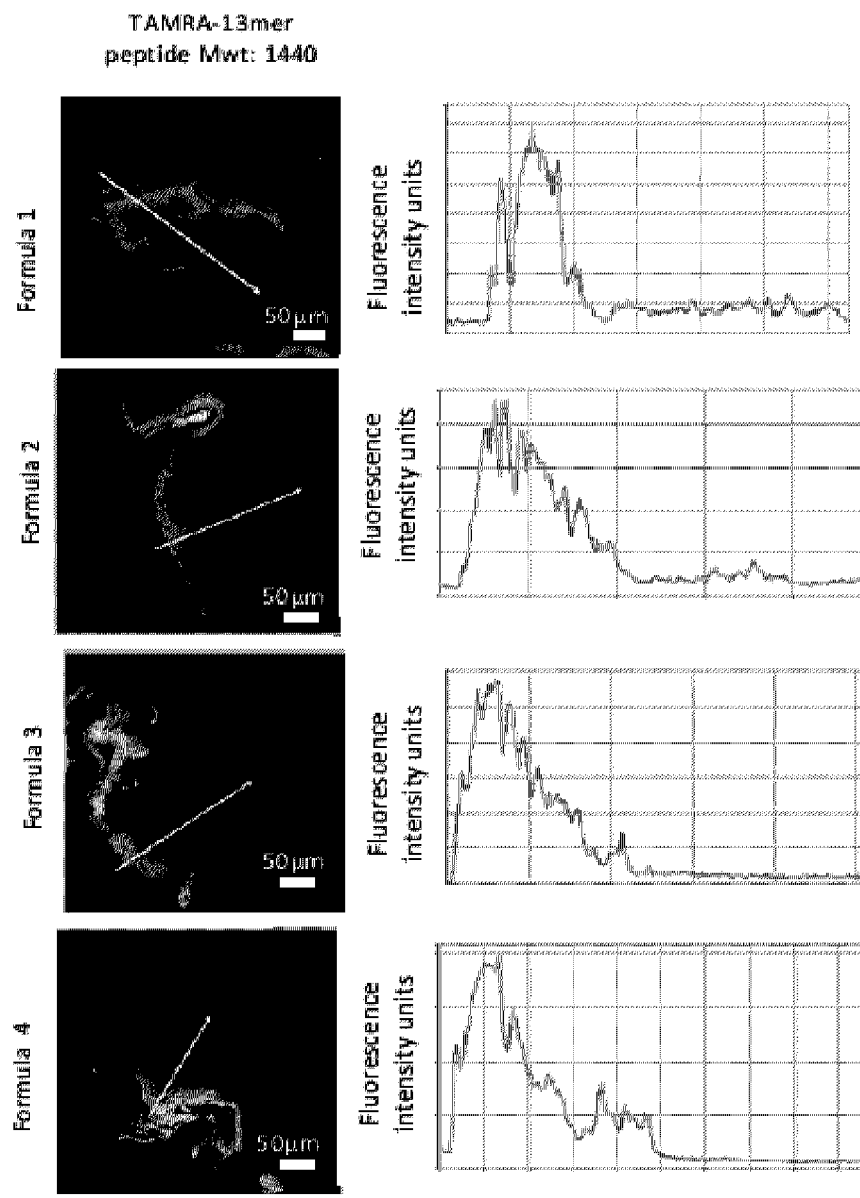
FIGS. 1A and B show confocal microscopic images of human skin treated with FIG. 1A) showing exemplary peptide lipid vesicle formulations 1-4 containing a rhodamine red labelled 12 mer peptide (molecular weight of peptide about 1200), FITC-insulin (molecular weight of insulin about 6,000) and FITC-IgG (molecular weight of IgG about 150,000)
Figure 1A:
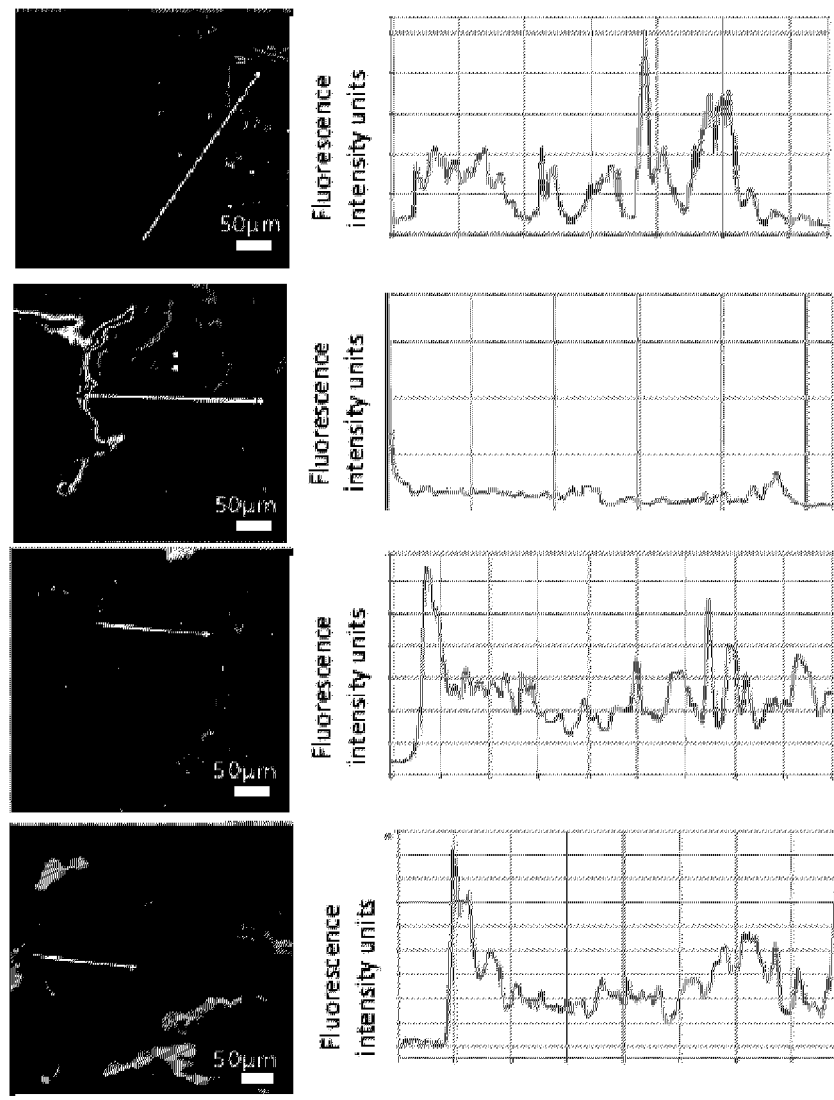
Figure 1A:
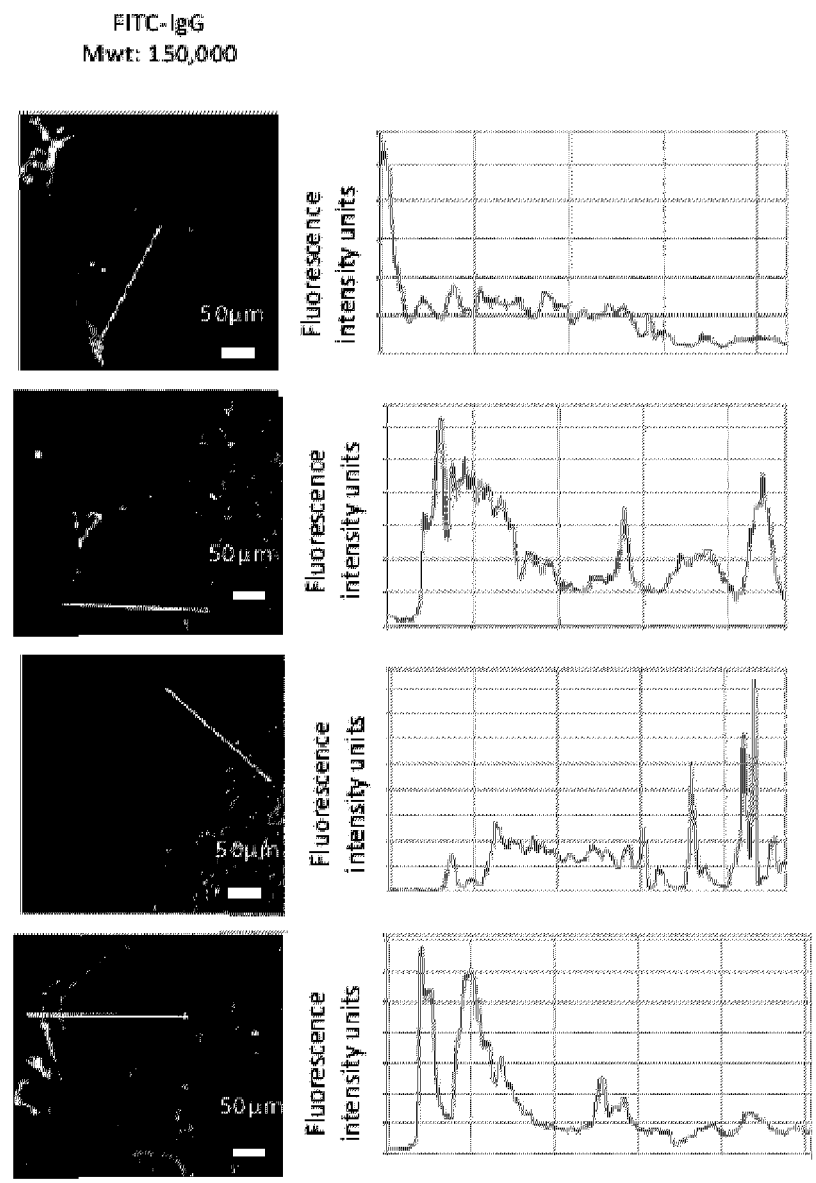
Figure 1B:
FIG. 1B) showing a separate control study with Alexa 647 labelled IgG (red fluorescence) incorporated into biphasic vesicles (comparative formula); the skin sections showed minimal fluorescence throughout the epidermis and dermis in the red channel, ie. first panel (the three panels: first panel: red channel for Alexa IgG; second panel: general tissue stain (blue nuclear stain Syto 60); third panel: merged image); last panel: placebo formulation treated skin (red channel and general tissue stain merged image) showing no fluorescence background at the settings used for analysis of protein delivery.

Unless otherwise indicated, the definitions and embodiments described in this and other sections are intended to be applicable to all embodiments and aspects of the present application herein described for which they are suitable as would be understood by a person skilled in the art.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

For example, as used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The phrase "consisting essentially of" will be understood to include those elements specifically recited and those additional elements that do not materially affect the basic and novel characteristics of the claimed technology. The phrase "consisting of" excludes any element not specified The term "and/or" as used herein means that the listed items are present, or used, individually or in combination. In effect, this term means that "at least one of" or "one or more" of the listed items is used or present. The term "and/or" with respect to enantiomers, prodrugs, salts and/or solvates thereof means that the compounds of the disclosure exist as individual enantiomers, prodrugs, salts and hydrates, as well as a combination of, for example, a salt of a solvate of a compound of the disclosure.

In embodiments comprising an "additional" or "second" component or effect, such as an additional or second compound, the second compound as used herein is different from the other compounds or first compound. A "third" compound is different from the other, first, and second compounds, and further enumerated or "additional" compounds are similarly different.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or illustrative language (e.g., "such as") provided herein, is intended merely to better illuminate the embodiments and does not pose a limitation on the scope of the claims unless otherwise stated. No language in the specification should be construed as indicating any non-claimed element as essential.

The term "hydrophilic" as used herein refers to a compound or additive that is substantially water soluble, water dispersible, or generally capable of absorbing and/or transmitting water.

The term "hydrophobic" as used refers to a compound or additive that is substantially non-soluble or dispersible in water.

The terms "nucleic acid" or "oligonucleotide", as used herein means two or more covalently linked nucleotides. Unless the context clearly indicates otherwise, the term generally includes, but is not limited to, deoxyribonucleic acid (DNA) and ribonucleic acid (RNA), which may be single-stranded (ss) or double stranded (ds). For example, the nucleic acid molecules or polynucleotides of the disclosure can be composed of single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically double-stranded or a mixture of single- and double-stranded regions. In addition, the nucleic acid molecules can be composed of triple-stranded regions comprising RNA or DNA or both RNA and DNA. The term "oligonucleotide" as used herein generally refers to nucleic acids up to 200 base pairs in length and may be single-stranded or double-stranded. The sequences provided herein may be DNA sequences or RNA sequences or hybrid sequences, however it is to be understood that the provided sequences encompass both DNA and RNA, as well as the complementary RNA and DNA sequences, unless the context clearly indicates otherwise. For example, the sequence 5'-GAATCC-3', is understood to include 5'-GAAUCC-3', 5'-GGATTC-3', and 5'GGAUUC-3'. The nucleic acid or oligonucleotide may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine as well as others. The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The nucleic acid can for example be plasmid DNA, a viral vector, naked DNA, RNA, DNA/RNA hybrids and synthetic nucleic acids and the like.

As used herein, the terms "peptide," "polypeptide," and "protein" refer to any chain of two or more natural or unnatural amino acid residues, regardless of post-translational modifications (e.g., glycosylation or phosphorylation). The polypeptides incorporated into the biphasic vesicles of the disclosure can include for example from 3 to 3500 natural or unnatural amino acid residues. Included are proteins that are a single polypeptide chain and multisubunit proteins (e.g. composed of 2 or more polypeptides).

The term "amino acid" includes all of the naturally occurring amino acids as well as modified L-amino acids. The atoms of the amino acid can for example include different isotopes. For example, the amino acids can comprise deuterium substituted for hydrogen, nitrogen-15 substituted for nitrogen-14, and carbon-13 substituted for carbon-12 and other similar changes.

An "immunogen" as used herein means a substance which when administered to a subject provokes an immune response and causes production of an antibody, activate lymphocytes or other reactive immune cells directed against an antigenic portion of the immunogen The term "antibody" as used herein is intended to include monoclonal antibodies, polyclonal antibodies, single chain, humanized and other chimeric antibodies as well as binding fragments thereof. The antibody may be from recombinant sources and/or produced in transgenic animals. Also included are human antibodies that can be produced through using biochemical techniques or isolated from a library. Humanized or chimeric antibody may include sequences from one or more than one isotype or class.

The term "binding fragment" as used herein refers to a part or portion of an antibody or antibody chain comprising fewer amino acid residues than an intact or complete antibody or antibody chain and which binds the antigen or competes with intact antibody. Exemplary binding fragments include without limitations Fab, Fab', F(ab')2, scFv, dsFv, ds-scFv, dimers, nanobodies, minibodies, diabodies, and multimers thereof. Fragments can be obtained via chemical or enzymatic treatment of an intact or complete antibody or antibody chain. Fragments can also be obtained by recombinant means. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be constructed by recombinant expression techniques.

Further, the definitions and embodiments described in particular sections are intended to be applicable to other embodiments herein described for which they are suitable as would be understood by a person skilled in the art. For example, in the following passages, different aspects are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The term "composition(s) of the disclosure" as used herein refers to a composition comprising biphasic lipid vesicles described herein.

The term "penetration enhancing agents" as used herein refers to one or more non-ionic surfactants having a hydrophilic-lipophilic balance (HLB) of about 10 or less or polycationic surfactants. In an embodiment, the one or more penetration enhancing agents are one or more non-ionic surfactants having a HLB of about 10 or less in combination with one or more penetration enhancing agents selected from one or more terpenes, alkaloids, salicylate derivatives, and polycationic surfactants and combinations thereof.

The term "entrapped" as used herein refers to the non-covalent association of the referred-to agent with a biphasic lipid vesicle's lipid bilayer or bilayers, the biphasic lipid vesicle's central core, and/or a space or spaces between adjacent bilayers of the biphasic lipid vesicle.

The term "biphasic lipid vesicle" as used herein refers to a vesicle whose central core compartment is occupied by an oil-in-water emulsion composed of an aqueous continuous phase and a dispersed hydrophobic, hydrophilic or oil phase. In an embodiment, the spaces between adjacent bilayers of the biphasic lipid vesicle may also be occupied by the emulsion.

The term "emulsion" as used herein refers to a mixture of two immiscible substances.

The term "bilayer" as used herein refers to a structure composed of amphiphilic lipid molecules arranged in two molecular layers, with the hydrophobic tails on the interior and the polar head groups on the exterior surfaces.

The term "topical administration" or "topical delivery" as used herein means intradermal, transdermal and/or transmucosal delivery of a compound by administration of a composition comprising the compound or compounds to skin and/or a mucosal membrane.

The term "gemini surfactant" as used herein refers to a surfactant molecule which contains more than one hydrophobic tail, and each hydrophobic tail having a hydrophilic head wherein he hydrophobic tails or hydrophilic heads are linked together by a spacer moiety. The hydrophobic tails can be identical or differ. Likewise, the hydrophilic heads can be identical or differ. the hydrophilic heads may be anionic, cationic, or neutral.

The term "HLB" or "Hydrophilic-Lipophilic Balance" value refers to standard HLB according to Griffin, J. Soc. Cosm. Chem., vol. 5, 249 (1954), which indicates the degrees of hydrophilicity and lipophilicity of a surfactant.

The term "subject" as used herein includes all members of the animal kingdom including mammals, and suitably refers to humans. Thus the methods and uses of the present application are applicable to both human therapy and cosmetic applications and veterinary applications.

The term "treating" or "treatment" as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with a skin disease, disorder or condition can be treated to prevent progression. Treatment methods comprise administering to a subject a therapeutically effective amount of one or more of the compounds of the disclosure and optionally consist of a single administration, or alternatively comprise a series of administrations.

As used herein, the term "effective amount" or "therapeutically effective amount" means an amount effective, at dosages and for periods of time necessary to achieve a desired result. The terms "to treat", "treating" and "treatment" as used herein and as is well understood in the art, means an approach for obtaining beneficial or desired results, including clinical results. "To treat", "treating" and "treatment" can also mean prolonging survival as compared to expected survival if not receiving treatment. "To treat", "treating" and "treatment" as used herein also include prophylactic treatment.

Where features or aspects of the disclosure are described in terms of Markush groups, those skilled in the art will recognize that the disclosure is also thereby described in terms of any individual member or subgroup of members of the Markush group.

Further, the definitions and embodiments described in particular sections are intended to be applicable to other embodiments herein described for which they are suitable as would be understood by a person skilled in the art. For example, in the following passages, different aspects are defined in more detail. Each aspect so defined may be combined with any other aspect or aspects unless clearly indicated to the contrary. For example, any combination of members of any group can be combined and optionally combined with any other subgroup of members. In particular, any feature indicated as being preferred or advantageous may be combined with any other feature or features indicated as being preferred or advantageous.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

II. Compositions of the Disclosure

The Applicant has shown that biphasic phospholipid vesicles having phospholipid bilayers that sequester a stabilized oil-in-water emulsion and a compound which include one or more penetration enhancing agents added to the phospholipid bilayers or the stabilized oil-in-water emulsion or both parts of the delivery system (e.g. compositions and/or other products comprising the biphasic vesicles described herein) provide enhanced skin penetration of the compound.

The Applicant has shown that certain penetration enhancing agents and combinations of penetration enhancing agents and compounds, relative to other combinations, can be used to more effectively deliver a higher quantity of the compound (e.g. in milligrams) into a quantity of skin (e.g. in grams).

The penetration enhancing agents compounds can be chosen from a wide variety of compounds generally known as penetration enhancers by themselves. In an embodiment, the Applicant has shown that penetration enhancing agents such as non-ionic surfactants having a hydrophilic-lipophilic balance ("HLB") of 10 or less or alone or combination of with one or more penetration enhancing agents such as terpenes, alkaloids, salicylate derivatives, polycationic (e.g. dicationic, tricationic etc) surfactants such as gemini cationic surfactants or polycationic amino acids, or combinations thereof provide enhanced skin penetration of the compound compared to an otherwise same or similar composition except in the absence of the one or more penetration enhancing agents.

In another embodiment, the Applicant has shown polycationic surfactants such as such as gemini dicationic surfactants or polycationic amino acids enhance skin penetration of the compound relative to otherwise same or similar composition except with a monocationic surfactant in place of the polycationic surfactant.

Accordingly, the present application includes a biphasic lipid vesicle composition comprising:
  a) lipid vesicles each comprising a lipid bilayer comprising vesicle forming lipids,
  b) an oil-in-water emulsion entrapped in the biphasic lipid vesicles, and stabilized by one or more surfactants;
  c) one or more compounds entrapped in the lipid bilayer or the oil-in-water emulsion of the biphasic vesicles); and
  d) one or more penetration enhancing agents entrapped in the lipid bilayer or the oil-in-water emulsion of the biphasic vesicles,
wherein the one or more penetration enhancing agents are one or more non-ionic surfactants having a hydrophilic-lipophilic balance (HLB) of about 10 or less.

In an embodiment, the biphasic lipid vesicle composition is a cosmetic composition. In an embodiment, the biphasic lipid vesicle composition is a pharmaceutical composition.

In an embodiment, a pharmaceutical composition (described herein as a lipid vesicle composition) is provided for the topical administration of a therapeutic compound to achieve topical delivery, the composition comprising: a lipid vesicle; an oil-in-water emulsion; the therapeutic compound; and one or more penetration enhancing agents; wherein the lipid vesicle comprises an exterior lipid bilayer; the oil-in-water emulsion is coated by the exterior lipid bilayer; the therapeutic compound is for example, a small molecule peptide or protein; and the one or more penetration enhancing agents increases a quantity of the therapeutic compound that absorbs into a quantity of skin relative to the composition in the absence of the one or more penetration enhancing agents.

The Applicant has shown that the lipid vesicles can be formulated to have the compound, and/or the penetration enhancing agents, selectively incorporated into the lipid bilayers and/or the oil-in-water emulsion at different stages of production of the biphasic lipid vesicles. The compound, for example, can be added only to the oil-in-water emulsion, only to the components of the lipid bilayers, or to both the oil-in-water emulsion and the lipid bilayers during production of the biphasic lipid vesicles. Similarly, the one or more penetration enhancing agents, can be added to only to the oil-in-water emulsion, only to the lipid bilayers, or to both the oil-in-water emulsion and the lipid bilayers during production of the biphasic lipid vesicles.

In an embodiment, the biphasic lipid vesicle composition is for the topical delivery of the one or more compounds. In an embodiment, the topical delivery is for intradermal, transdermal, mucosal or transmucosal delivery.

In an embodiment, the biphasic lipid vesicle composition comprises a suspension of the biphasic lipid vesicles.

In an embodiment, the one or more penetration enhancing agents are entrapped in the oil-in-water emulsion of the biphasic lipid vesicle. In an embodiment, the oil-in-water emulsion of the biphasic lipid vesicles comprises about 0.01 wt % to about 20 wt % of one or more penetration enhancing agents. In an embodiment, the oil-in-water emulsion of the biphasic lipid vesicle comprises about 0.1 wt % to about 10 wt % of one or more penetration enhancing agents. In an embodiment, the oil-in-water emulsion of the biphasic lipid vesicle comprises about 0.5 wt % to about 9 wt %, about 0.5 wt % to about 8 wt %, about 0.5 wt % to about 7 wt %, about 1 wt % to about 6 wt %, about 1 wt % to about 5 wt %, about 1 wt % to about 4 wt %, about 1 wt % to about 3 wt %, or about 1 wt % to about 2 wt %, of one or more penetration enhancing agents.

In an embodiment, the one or more penetration enhancing agents are entrapped in the lipid bilayer of the lipid vesicle. In an embodiment, the lipid bilayer of the lipid vesicle composition comprises 0.1 wt % to 20 wt % of the one or more penetration enhancing agents. In an embodiment, the lipid bilayer comprises 0.1 wt % to 10 wt % of the one or more skin penetration enhancing agents. In an embodiment, the lipid bilayer of the biphasic lipid vesicle comprises about 7 wt % of one or more skin penetration enhancing agents. In an embodiment, the lipid bilayer of the lipid vesicle comprises about 10 wt %, about 9 wt %, about 8 wt %, about 7 wt %, about 6 wt %, about 5 wt %, about 4 wt %, about 3 wt %, about 2 wt %, about 1 wt %, about 0.5 wt % or about 0.1 wt % of one or more skin penetration enhancing agents.

In an embodiment, the one or more penetration enhancing agents are entrapped in both the lipid bilayer and the oil-in-water emulsion of the biphasic lipid vesicle.

In an embodiment, the penetration enhancing agents are one or more non-ionic surfactants having a hydrophilic-lipophilic balance (HLB) of about 10 or less selected from one or more of polyethylene glycol ethers of fatty alcohols, sorbitan esters, polysorbates, sorbitan esters and polyethylene glycol fatty acid esters and combinations thereof.

In an embodiment, the polyethylene glycol ethers of fatty alcohols are selected from Ceteth-2®, Steareth-2®, Oleth 2®, Oleth-3®, and Oleth-5® and combinations thereof. In an embodiment, the polyethylene glycol ethers of fatty alcohols are selected from Oleth 2®, Oleth-3®, and Oleth-5®. In an embodiment, the polyethylene glycol ethers of fatty alcohols is Oleth 2®.

In an embodiment, the sorbitan esters are selected from sorbitan monolaurate, sorbitan monopalmitate, sorbitan monostearate, sorbitan monooleate, sorbitan trioleate, sorbitan sesquioleate, and sorbitan Isostearate, and combinations thereof. In an embodiment, the sorbitan esters are selected from sorbitan monolaurate, sorbitan monopalmitate, and sorbitan monostearate, and combinations thereof. In an embodiment, the sorbitan esters is sorbitan monopalmitate.

In an embodiment, the polyethylene glycol fatty acid esters are selected from one or more PEG-8 dilaurate, PEG-4 dilaurate, PEG-4 laurate, PEG-8 dioleate, PEG-8 distearate, PEG-8 distearate, PEG-7 glyceryl cocoate, and PEG-20 almond glycerides and combinations thereof. In an embodiment, the polyethylene glycol fatty acid esters are selected from PEG-4 dilaurate, and PEG-4 laurate and combinations thereof. In an embodiment, the polyethylene glycol fatty acid esters is PEG-4 dilaurate.

In an embodiment, the one or more non-ionic surfactants having a hydrophilic-lipophilic balance (HLB) of about 10 or less are further selected from propylene glycol isostearate, glycol stearate, glyceryl stearate, glyceryl stearate SE, glyceryl laurate, glyceryl caprylate, PEG-30 dipolyhydroxystearate, glycol distearate and combinations thereof.

In an embodiment, the one or more non-ionic surfactants having a hydrophilic-lipophilic balance (HLB) of about 10 or less are selected from the surfactants in in Table 1:

TABLE 1

| Category | INCI/Chemical name | Properties |
| --- | --- | --- |
| | Ceteth-2 ® (Diethylene glycol hexadecyl ether) | HLB = 5.3 |
| | Steareth- ® (2-(2-octadecoxy-ethoxy)ethanol) | HLB = 4.9 |
| | Oleth-2 ® (Polyoxyethylene (2) Oleyl Ether/Diethylene glycol monooleyl ether) | HLB = 4.9 |
| | Oleth-3 ® (Polyoxyethylene (3) Oleyl Ether) | HLB = 6.6 |
| | Oleth-5 ® (Polyoxyethylene (5) Oleyl Ether) | HLB = 9 |
| | Polysorbate 61 ® | HLB = 9.6 |
| | Sorbitan monolaurate | HLB = 8.6 |
| | Sorbitan monopalmitate | HLB = 6.7 |
| | Sorbitan monostearate | HLB = 4.7 |
| | Sorbitan monooleate | HLB = 4.3 |
| | Sorbitan trioleate | HLB = 1.8 |
| | Sorbitan sesquioleate | HLB = 3.7 |
| | Sorbitan Isostearate | HLB = 4.7 |
| | PEG-8 dilaurate | HLB = 10 |
| | PEG-4 dilaurate (Polyoxyethylene (8) dilaurate) | HLB = 6 |
| | PEG-4 laurate ((Polyoxyethylene (4) dilaurate) | HLB = 9 |
| | PEG-8 dioleate | HLB = 7.2 |
| | PEG-8 distearate | HLB = 8 |
| | PEG-7 glyceryl cocoate | HLB = 10 |
| | PEG-20 almond glycerides | HLB = 10 |
| | Propylene glycol isostearate | HLB = 2.5 |
| | Glycol stearate | HLB = 2.9 |
| | Glyceryl stearate | HLB = 3.8 |
| | Glyceryl stearate SE | HLB = 5.8 |

TABLE 1-continued

| Category | INCI/Chemical name | Properties |
|---|---|---|
| | Glyceryl laurate | HLB = 5.2 |
| | Glyceryl caprylate | HLB = 5-6 |
| | PEG-30 dipolyhydroxy-stearate | HLB = 5.5 |
| | Glycol distearate | HLB = 1, and |
| | Phospholipid/lecithin and combinations thereof. | HLB = 4-10 |

In an embodiment, the one or more penetration enhancing agents are one or more non-ionic surfactants having a HLB of about 10 or less in combination with one or more penetration enhancing agents selected from one or more terpenes, alkaloids, salicylate derivatives, and di- or polycationic surfactants and combinations thereof.

In an embodiment, the one or more non-ionic surfactants having a HLB of about 10 or less are as described above.

In an embodiment, the one or more terpenes are selected from one or more eugenol, d-limonene, menthol, menthone, farnesol, neridol, camphor, nerol and thymol, and combinations thereof. In an embodiment, the one or more terpenes are selected from one or more of menthol, camphor, nerol and thymol, and combinations thereof.

In an embodiment, the one or more salicylate derivatives is selected from ethyl salicylate, salicylic acid, acetylsalicylic acid and trolamine salicylate. In an embodiment, the salicylate derivative is methyl salicylate.

In an embodiment, the one or more alkaloids are selected from piperidine derivatives (e.g., piperine and lobeline), purine derivative (e.g., caffeine, theobromine and theophylline), pyridine derivative (e.g., nicotine), colchicine, pyrrolidine derivative (e.g., N-methyl pyrrolidone and hygrine), benzylamine (e.g., capsaicin), isoquinoline derivative (e.g., berberine and sanguinarine) or an imidazole derivative (e.g., histamine and pilocarpine). In an embodiment, the one or more alkaloids are piperidine derivatives. In an embodiment, the one or more alkaloids are piperine or lobeline, or combinations thereof. In an embodiment, the one or more alkaloids is piperine.

In an embodiment, the polycationic surfactants are one or more gemini surfactants.

A gemini surfactant is a surfactant molecule which contains more than one hydrophobic tail. Each hydrophobic tail has a hydrophilic head (Menger and Keiper, 2000; Kirby et al., 2003). The hydrophobic tails or hydrophilic heads are linked together by a spacer. The hydrophobic tails can be identical or differ. Likewise, the hydrophilic heads can be identical or differ. Further, the hydrophilic heads may be anionic (e.g. of a phosphate, sulphate or carboxylate type), cationic (e.g. of a quaternary ammonium type), or neutral (e.g. of a polyether, peptide or sugar type) (Menger and Keiper, 2000). In aqueous solutions, gemini surfactants spontaneously aggregate into micelles whose shape and size are particularly sensitive to the length and hydrophobic or hydrophilic nature of the spacer. The spacer can be variable, namely short (e.g., 2 methylene groups) or long (e.g., more than 12 methylene groups); rigid (e.g., stilbene) or flexible (e.g., methylene chain); and polar (e.g., polyether, ethoxyl or polyethoxyl) or nonpolar (e.g., aliphatic, aromatic) (Menger and Keiper, 2000). As the hydrophobic tails, hydrophilic heads and spacer can vary with regard to the above aspects, innumerable different molecules can be designed.

In an embodiment, the type of hydrophobic tail is a $C_3$-$C_{30}$ alkyl group, linear or branched, saturated or unsaturated. In an embodiment, the hydrophilic heads may be anionic, cationic or neutral. In an embodiment, the hydrophilic heads are cationic.

In an embodiment, the gemini surfactants anionic, cationic or neutral. In an embodiment, the polycationic surfactants are one or more gemini dicationic surfactants.

In an embodiment, the gemini surfactants comprise a linear hydrocarbon tailgroups and quaternary ammonium headgroups. The general structure of one type of gemini cationic surfactant includes a head group composed of two positively charged nitrogen atoms, separated by a spacer (n) of 3, 4, 6, 8, 10, 12, or 16 carbon atoms and each containing two methyl groups, and the tails consist of two saturated 12 or 16 carbon atom chains (m=10 or 14), respectively.

In an embodiment, the one or more gemini dicationic surfactants are of a quaternary ammonium type. In an embodiment, the one or more gemini dicationic surfactants are selected from the group consisting of 12-7NH-12, 12-7NCH$_3$-12, 16-3-16, 12-4(OH)$_2$-12, and 12-EO1-12. In an embodiment, the one or more gemini cationic surfactants are selected from the group consisting of 12-7NH-12, 12-7NCH$_3$-12, and 16-3-16.

In an embodiment, the one or more polycationic surfactants are polycationic amino acids. In an embodiment, the polycationic amino acids are selected from polylysine, polyarginine and combinations thereof.

In an embodiment, the one or more penetration enhancing agents are one or more non-ionic surfactants having a HLB of about 10 or less in combination with one or more penetration enhancing agents selected from one or more terpenes, alkaloids, and salicylate derivatives.

In an embodiment, the biphasic lipid vesicle composition comprises one to six penetration enhancing agents. In an embodiment, the biphasic lipid vesicle composition comprises one to four penetration enhancing agents. In an embodiment, the biphasic lipid vesicle composition comprises one to three penetration enhancing agents.

In an embodiment, the penetration enhancing agents are one or more non-ionic surfactants having a HLB of about 9 or less, about 8 or less, about 7 or less, or about 6 or less and optionally having a HLB of 1 or more, 2 or more, 3 or more or 4 or more or any combination thereof e.g. about 7 or less and about 3 or more. In an embodiment, the penetration enhancing agents are one or more non-ionic surfactants having a HLB of about 1 to about 10, about 1 to about 9, about 2 to about 8, about 3 to about 7, or about 4 to about 7. In an embodiment, the penetration enhancing agents are one or more non-ionic surfactants having a hydrophilic-lipophilic balance (HLB) of, about 3 to about 7, or about 4 to about 7. In an embodiment, the penetration enhancing agents are one or more non-ionic surfactants having a HLB of about 4 to about 7.

In an embodiment, the penetration enhancing agent is Oleth-2® (diethylene glycol monooleyl ether). In an embodiment, the penetration enhancing agents are Oleth-2® in combination with one or more terpenes. In an embodiment, the penetration enhancing agents are Oleth-2® in combination with one or more of menthol, camphor, nerol or thymol, or combinations thereof. In an embodiment, the penetration enhancing agents are Oleth-2® in combination with menthol, or camphor or combinations thereof. In an embodiment, the penetration enhancing agents are Oleth-2® in combination with menthol and camphor. In an embodiment, the penetration enhancing agents are Oleth-2® in combination with nerol. In an embodiment, the penetration enhancing agents are Oleth-2® in combination with thymol. In an embodiment, the penetration enhancing agents are Oleth-2® in combination with nerol. In an embodiment, the penetration enhancing agents are Oleth-2® in combination with methyl salicylate. In an embodiment, the penetration enhancing agents are Oleth-2® in combination with one or more alkaloids. In an embodiment, the penetration enhancing agents are Oleth-2® in combination with piperidine.

In an embodiment, the one or more non-ionic surfactants having a HLB of about 10 or less is entrapped in the lipid bilayer, and the one or more terpenes or the one or more alkaloids are entrapped in the lipid bilayer, the oil-in-water emulsion or both.

In an embodiment, the one or more penetration enhancing agent is PEG-4 dilaurate. In an embodiment, the one or more penetration enhancing agents are PEG-4 dilaurate in combination one or more alkaloids. In an embodiment, the one or more penetration enhancing agents are PEG-4 dilaurate in combination with piperidine. In an embodiment, the one or more penetration enhancing agents are PEG-4 dilaurate in combination with methyl salicylate.

In an embodiment, the PEG-4 dilaurate is entrapped in the lipid bilayer, and the one or more alkaloids or the methyl salicylate are entrapped in the lipid bilayer, the oil-in-water emulsion or both.

In an embodiment, the one or more penetration enhancing agents are Oleth-2, PEG-4 dilaurate or sorbitan monopalmitate, or combinations thereof. In an embodiment, the one or more penetration enhancing agents are Oleth-2 and sorbitan monopalmitate in combination. In an embodiment, the one or more penetration enhancing agents are PEG-4 dilaurate and sorbitan monopalmitate in combination.

In an embodiment, the Oleth-2®, PEG-4 dilaurate or sorbitan monopalmitate, or combinations thereof are entrapped in the lipid bilayer, the oil-in-water emulsion or both.

In an embodiment, the one or more penetration enhancing agents increases a quantity of a compound that absorbs into a quantity of skin by at least 10%, 20%, 30%, 40%, or 50% relative to an otherwise same or similar composition except in the absence of the one or more penetration enhancing agents. In an embodiment, the one or more penetration enhancing agents increases a quantity of a compound that absorbs into a quantity of skin by at least about 10%, about 15%, about 20%, about 25%, about 30%, about 35%, about 40%, about 45% or about 50% relative to an otherwise same or similar composition except in the absence of the one or more penetration enhancing agents.

In an embodiment, biphasic lipid vesicle comprises from about 0.1 wt % to about 5 wt % of the alkaloid. In an embodiment, biphasic lipid vesicle comprises from about 0.1 wt % to about 4 wt % of the alkaloid. In an embodiment, the biphasic lipid vesicle comprises from about 0.1 wt % to about 3 wt % of the alkaloid. In an embodiment, the biphasic lipid vesicle comprises from about 1 wt % to about 3 wt % of the alkaloid. In an embodiment, the lipid bilayer of the lipid vesicle comprises from 1 wt % to 5 wt % of the alkaloid. In some embodiments, the alkaloid is entrapped in the lipid bilayer of the biphasic lipid vesicle.

Generally, the biphasic lipid vesicle is a multilamellar lipid vesicle, further comprising one or more interior lipid bilayers. The multilamellar biphasic lipid vesicles that have multiple concentric lipid bilayer shells that encapsulate an oil-in-water emulsion.

In an embodiment, the oil-in-water emulsion includes droplets having an average diameter of less than 1 µm. In an embodiment, the average diameter of the oil-in-water emulsion droplets may be less than 0.5 µm, 0.25 µm, 0.1 µm or 0.01 µm. In an embodiment, the average diameter of the oil-in-water emulsion droplets may be less than about 0.5 µm, less than about 0.25 µm, less than about 0.1 µm or less than about 0.01 µm. Because the oil-in-water emulsion includes aqueous and non-aqueous regions these submicron oil-in-water emulsion droplets can be tuned to incorporate hydrophilic and hydrophobic compounds and excipients.

In an embodiment, the oil-in-water emulsion comprises from 40 wt % to 99.9 wt % water. In an embodiment, the oil-in-water emulsion includes 10 wt % to 95 wt % water, such as 10 wt % to 25 wt %, 25 wt % to 50 wt %, 50 wt % to 75 wt %, 75 wt % to 95 wt % water. In an embodiment, the oil-in-water emulsion comprises from about 10 wt % to about 99.9 wt % water, from about 15 wt % to about 99.9 wt % water, from about 25 wt % to about 99.9 wt % water, from about 25 wt % to about 50 wt % water, from about 40 wt % to about 99 wt % water, from about 50 wt % to about 95 wt % water, from about 50 wt % to about 75 wt % water, from about 75 wt % to about 95 wt % water.

In an embodiment, the oil-in-water emulsion comprises from 0.1 wt % to 60 wt % of an oil. In an embodiment, the oil-in-water emulsion comprises from about 0.1 wt % to about 60 wt % of an oil, from about 0.5 wt % to about 50 wt % of an oil, from about 1 wt % to about 40 wt % of an oil or from about 1 wt % to about 20 wt % of an oil.

In an embodiment, the oil-in-water emulsion may account for up to about 95 wt % of the biphasic lipid vesicle. In other words, in an embodiment, the biphasic lipid vesicle comprises from about 1 wt % to about 95 wt % of the oil-in-water emulsion. In an embodiment, the lipid vesicle composition may include 1 wt % to 10 wt %, 20 wt % to 30 wt %, 30 wt % to 40 wt %, 40 wt % to 95 wt % of the oil-in-water emulsion. In an embodiment, the lipid vesicle comprises from about 1 wt % to about 10 wt %, from about 20 wt % to about 30 wt %, from about 30 wt % to about 40 wt %, from about 40 wt % to about 95 wt %, from about 50 wt % to about 95 wt %, from about 60 wt % to about 95 wt % or from about 70 wt % to about 95 wt % of the oil-in-water emulsion.

In an embodiment, the oil in the oil-in-water emulsion is selected from the group consisting of vegetable oils, mono-, di- and triglycerides, silicone fluids and mineral oils, and combinations thereof. It would be appreciated that the oil-in-water emulsion can be adjusted to have various quantities of water and oil to optimize the solubility of any given compound, compound, penetration enhancer compounds, surfactants and/or emulsifiers, etc.

The oil-in-water emulsion of the biphasic lipid vesicles is stabilized by one or more surfactants. In an embodiment, the oil-in-water emulsion of the biphasic lipid vesicles comprises from 0.01 wt % to 40 wt % of the one or more surfactants. Without being bound by theory, it is contemplated that the surfactants can be added to the oil-in-water emulsion to modify the stability of the oil-in-water emulsion. In an embodiment, the water-in-oil emulsion comprises 0.01 wt % to 10 wt %, 10 wt % to 20 wt % or 20 wt % to 40 wt % of the one or more surfactants. In an embodiment, the water-in-oil emulsion comprises about 0.01 wt % to about 40 wt %, about 0.01 wt % to about 10 wt %, about 10 wt % to about 20 wt %, about 20 wt % to about 30 wt % about 20 wt % to about 40 wt %, or about 30 wt % to about 40 wt % of the one or more surfactants.

In an embodiment, the oil-in-water emulsion of the biphasic lipid vesicles is stabilized by one or more surfactants selected from the group consisting of a polyethylene glycol ether of a fatty alcohol, polyethylene glycol fatty acid ester, polysorbate and a sorbitan ester. In an embodiment, the one or more surfactants have an average hydrophilic-lipophilic balance (HLB) number greater than 10 or more. In an embodiment, the one or more surfactants in the oil-in-water emulsion have a HLB of greater than 10 or more, about 11 or more, about 12 or more, about 13 or more, about 14 or more, about 15 or more, about 16 or more, about 17 or more, about 18 or more, about 19 or more or about 20 or more or combinations thereof. In an embodiment, the one or more surfactants in the oil-in-water emulsion have a HLB of greater than 10 to about 20, about 10 to about 18, about 10 to about 16, or about 10 to about 15. In an embodiment, the one or more surfactants in the oil-in-water emulsion have a HLB of about 10 to about 16. In an embodiment, the one or more surfactants in the oil-in-water emulsion have a HLB of, 10-20 or 10-16.

In an embodiment, the one or more non-ionic surfactants having a hydrophilic-lipophilic balance (HLB) greater than 10 or more are selected from the surfactants in in Table 2:

rather the one or more non-ionic surfactants having a hydrophilic-lipophilic balance (HLB) of about 10 or less of the penetration enhancing agents is used as an additional surfactant to the stabilizing surfactant to provide the permeation enhancing effect.

It would also be appreciated that relative to known biphasic vesicle compositions where the lipid vesicles contained a surfactant as a stabilizing structural ingredient for the creation of oil-in-water emulsion, the present disclosure uses one or more penetration enhancing agents that, when incorporated into the vesicle structure (either lipid bilayer or oil-in-water emulsion) provide enhanced delivery capabilities for a range of compounds.

In an embodiment, the oil-in-water emulsion comprises from 10 wt % to 99 wt % water, from 0.5 wt % to 60 wt % oil and further comprise from 0.01 wt % to 20 wt % of one or more surfactants for stabilizing the oil-in-water emulsion.

TABLE 2

| Trade name | INCI/Chemical name | Properties |
|---|---|---|
| Polyethylene glycol ethers of fatty alcohols | | |
| BRIJ™ 35Brij™ L23 | Laureth-23 (Polyoxyethylene (23) lauryl ether) | HLB = 17.0 |
| Brij 56/Brij™ C10 | Ceteth-10 (polyoxyethylene (10) cetyl ether) | HLB = 12.9 |
| BRIJ™ 58/Brij™ C20 | Ceteth-20 (polyoxyethylene (20) cetyl ether) | HLB = 15.7 |
| BRIJ™ 700 | Steareth-100 (polyoxyethylene (100) stearyl ether) | HLB = 18.8 |
| BRIJ™ 721 | Steareth-21 (polyoxyethylene (21) stearyl ether) | HLB = 15.5 |
| BRIJ™ 76 | Steareth-10 (polyoxyethylene (10) stearyl ether) | HLB = 12.4 |
| BRIJ™ 78 | Steareth-20 (polyoxyethylene (20) stearyl ether) | HLB = 15.3 |
| Brij™ CS20 | Ceteareth-20 | HLB = 15.2 |
| Brij™ IC20 | Isoceteth-20 | HLB = 15.7 |
| Brij 97Brij™ O10 | Oleth-10 | HLB = 12.4 |
| Brij 98Brij™ O20 | Oleth-20 | HLB = 15.3 |
| Polysorbates | | |
| Tween20 | Polysorbate 20 | HLB = 16.7 |
| Tween 21 | Polysorbate 21 | HLB = 13.3 |
| Tween 40 | Polysorbate 40 | HLB = 15.6 |
| Tween 60 | Polysorbate 60 NF | HLB = 14.9 |
| Tween 80 | Polysorbate 80/ polyoxyethylene 20 sorbitan monooleate | HLB = 15 |
| Tween 85 | Polysorbate 85 | HLB = 11 |
| Polyethylene glycol fatty acid esters | | |
| Lipopeg 4-L | PEG-8 laurate | HLB = 13 |
| Lipopeg 4-S/Myrj 45 | PEG-8 stearate | HLB = 11.2 |
| Lipopeg 10-S/Myrj 49 | PEG-20 stearate | HLB = 15.2 |
| Lipopeg 39-S/Myrj 52 | PEG-40 stearate | HLB = 16.9 |
| Lipopeg 100-S/Myrj 59 | PEG-100 stearate | HLB = 18.8 |
| Lipopeg 6000-DS | PEG-150 distearate | HLB = 18.4 |
| | PEG-25 Hydrogenated Castor Oil | HLB = 10.8 |
| | PEG-7 Olivate | HLB = 11 |
| | PEG-8 Oleate | HLB = 11.6 |
| | Stearamide MEA | HLB = 11 |
| | Cetearyl Glucoside | HLB = 11 |
| | Polyglyceryl-3 Methyglucose Distearate | HLB = 12 |
| | Cocamide MEA | HLB = 13.5 |
| | Isosteareth-20 | HLB = 15 |
| | PEG-60 Almond Glycerides | HLB = 15 |
| | Laureth-23 | HLB = 16.9 |
| | PEG-100 Stearate | HLB = 18.8 |
| | Steareth-100 | HLB = 18.8 |
| | PEG-80 Sorbitan Laurate | HLB = 19.1 |

In an embodiment, oil-in-water emulsion of the biphasic lipid vesicles is stabilized by one or more surfactants selected from Ceteth-10® and Tween 80® (polysorbate 80 (glycol)/polyoxyethylene 20 sorbitan monooleate).

The one or more non-ionic surfactants having a hydrophilic-lipophilic balance (HLB) of about 10 or less of the penetration enhancing agents is not employed for the stabilization and emulsification of the oil-in-water emulsion, but In an embodiment, the vesicle forming lipids are amphipathic lipids having a hydrophobic tail and a head group which can form spontaneously into bilayer vesicles in water. In an embodiment, the vesicle-forming lipids comprise two hydrocarbon chains, such as acyl chains, where the head group is either polar or nonpolar. In an embodiment, the vesicle forming lipids are selected from one or more of phospholipids, glycolipids, lecithins, and ceramides such as phosphatidylethanolamine, lysolecithin, lysophosphatidylethanolamine, phosphatidylserine, phosphatidylinositol, sphingomyelin, cardiolipin, phosphatidic acid, and cerebroside. These lipids can be obtained commercially or prepared according to published methods.

In an embodiment, the vesicle forming lipids are phospholipids. In an embodiment, the phospholipids are one or more esters of glycerol with one or two (equal or different) residues of fatty adds and with phosphoric acid, wherein the phosphoric acid residue is in turn bound to a hydrophilic group, such as, for instance, choline (phosphatidylcholines—PC), serine (phosphatidylserines—PS), glycerol (phosphatidylglycerols—PG), ethanolamine (phosphatidylethanolamines—PE), or inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing 12 to 24 carbon atoms, or 14 to 22 carbon atoms; the aliphatic chain may contain one or more unsaturations or is completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Saturated fatty acids such as myristic acid, palmitic acid, stearic acid and arachidic acid may be employed.

In an embodiment, the phospholipids are phosphatidic acids, i.e., the diesters of glycerol-phosphoric acid with fatty acids; sphingolipids such as sphingomyelins, i.e., those phosphatidylcholine analogs where the residue of glycerol diester with fatty acids is replaced by a ceramide chain; cardiolipins, i.e., the esters of 1,3-diphosphatidylglycerol with a fatty acid; glycolipids such as gangliosides GM1 (or GM2) or cerebrosides; glucolipids; sulfatides and glycosphingolipids.

In an embodiment the phospholipids are naturally occurring, semisynthetic or synthetically prepared products that can be employed either singularly or as mixtures. In an embodiment, the naturally occurring phospholipids are natural lecithins (phosphatidylcholine (PC) derivatives) such as, typically, soya bean or egg yolk lecithins.

In an embodiment, the semisynthetic phospholipids are the partially or fully hydrogenated derivatives of the naturally occurring lecithins. In an embodiment, the phospholipids include fatty acids di-esters of phosphatidylcholine, ethylphosphatidylcholine, phosphatidylglycerol, phosphatidic acid, phosphatidylethanolamine, phosphatidylserine or of sphingomyelin. In an embodiment, the phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroylphosphatidylglycerol (DLPG) and its alkali metal salts, diarachidoylphosphatidylglycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoylphosphatidylethanolamine (DMPE), dipalmitoylphosphatidylethanolamine (DPPE), distearoyl phosphatidyl-ethanolamine (DSPE), dioleylphosphatidylethanolamine (DOPE), diarachidoylphosphatidylethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoylphosphatidylinositol (DOPI).

In an embodiment, the, the phospholipid is dioleoylphosphatidyl ethanolamine (DOPE) phosphatidylethanolamine (cephalin) (PE), phosphatidic acid (PA), phosphatidylcholine (PC), 1,2-distearoyl-sn-glycero-3-phosphoethanolamine (DSPE) or phosphatidylserine (PS).

In an embodiment, the biphasic lipid vesicle of the biphasic lipid vesicle compositions generally comprises 0.1 wt % to 30 wt % phospholipids. In some embodiments, the lipid vesicle comprises 1 wt % to 10 wt %, 10 wt % to 20 wt %, 20 wt % to 30 wt % of the phospholipids. In some embodiments, the biphasic lipid vesicle comprises 9 wt % to 13 wt % phospholipids. In some embodiments, the biphasic lipid vesicle comprises 10 wt % phospholipids. In some embodiments, the biphasic lipid vesicle comprises 12 wt % phospholipids. In some embodiments, the biphasic lipid vesicle comprises about 1 wt % to about 10 wt %, about 10 wt % to about 20 wt %, about 20 wt % to about 30 wt %, about 9 wt % to about 13 wt % phospholipids, about 13 wt %, about 12 wt %, about 11 wt % %, or about 10 wt % of phospholipids.

In an embodiment, the one or more compounds are entrapped in oil-in-water emulsion of the biphasic lipid vesicle. In an embodiment, the oil-in-water emulsion comprises from 1 ng/g to 1,000 ng/g of the compound/oil-in-water emulsion. In an embodiment, the oil-in-water emulsion comprises from 1 ng/g to 10 ng/g, from 10 ng/g to 100 ng/g or from 100 ng/g to 1,000 ng/g of the compound/oil-in-emulsion.

In an embodiment, the oil-in-water emulsion droplets comprise 0.0000001 wt % to 0.0001 wt %, 0.0001 wt % to 0.1 wt %, 0.1 wt % to 1 wt %, or 1 wt % to 10 wt % of the compound. In an embodiment, the oil-in-water emulsion comprise about 0.0000001 wt % to about 0.0001 wt %, about 0.0001 wt % to about 0.1 wt %, about 0.1 wt % to about 1 wt %, or about 1 wt % to about 10 wt % of the compound. In an embodiment, the oil-in-water emulsion comprises from 0.0000001 wt % to 10 wt % of the compound.

In an embodiment, the one or more compounds are entrapped in the lipid bilayer of the biphasic lipid vesicle. In an embodiment, the lipid bilayers of the lipid vesicle compositions can be formulated to have one or more compounds. In an embodiment, the lipid bilayer of the lipid vesicle composition comprises 0.0000001 wt % to 10 wt % of the compound. In an embodiment, the lipid bilayer comprises about 0.0000001 wt % to about 0.0001 wt %, about 0.0001 wt % to about 0.1 wt %, about 0.1 wt % to about 1 wt %, or about 1 wt % to about 10 wt % of the compound. In an embodiment, the lipid bilayer of the lipid vesicle comprises 1 wt % to 3 wt % of the compound.

In an embodiment, the one or more compounds are entrapped in both the lipid bilayer and the oil-in-water emulsion of the biphasic lipid vesicle. In an embodiment, the one or more compounds entrapped in the lipid bilayer are the same as the one or more compounds entrapped in the oil-in-water emulsion of the biphasic lipid. In an embodiment, the one or more compounds entrapped in the lipid bilayer are different from the one or more compounds entrapped in the oil-in-water emulsion of the biphasic lipid vesicle.

It would be appreciated, for example, that one or more compound entrapped in the oil-in-water emulsion would have a faster rate of release than the same one or more compounds entrapped in the lipid bilayer.

In an embodiment, the one or more compounds are selected from but not limited to, small molecules, proteins, peptides, carbohydrates, nucleic acids, vaccine antigens, and/or plant extracts.

In an embodiment, the one or more compound are therapeutic compounds. Therefore, the composition of the disclosure is a pharmaceutical composition.

In an embodiment, the small molecules are prostaglandins, anesthetic agents such as ibuprofen and diclofenac, analgesics or sedatives including opioids such as, for example, buprenorphine, fentanyl, sufentanil, alfentanil and remifentanil, cardioactive medication, androgenic steroids, estrogens, progestogens, antihistamines antiviral agents, vitamins, anti-inflammatory agents, antifungal agents, corticosteroids, vitamins, anti-infectives, dermatological agents, medication for the treatment of nausea and sickness amino acids, short peptides (upto 1000 Da), carbohydrates or natural compounds and combinations thereof.

In an embodiment, the cardioactive medication is organic nitrates, such as nitroglycerin, isosorbide dinitrate and/or isosorbide mononitrate, quinidine sulphate, procainamide, thiazides such as bendroflumethiazide, chlorothiazide and/or hydrochlorothiazide, nifedipine, nicardipine, adrenergic blockers such as timolol and/or propranolol, verapamil, diltiazem, captopril, clonidine or prazosine.

In an embodiment, the androgenic steroids are testosterone, methyltestosterone or fluoxymesterone.

In an embodiment, the estrogens are estradiol valerate, equilin, mestranol, estrone, estriol, 17.beta.-ethinylestradiol or diethylstilbestrol.

In an embodiment, the antihistamines are diphenhydramine, dimenhydrinate, perphenazine, triprolidine, pyrilamine, chlorcyclizine, promethazine, carbinoxamine, tripelennamine, brompheniramine, clorprenaline, terfenadine and/or chlorpheniramine;

In an embodiment, the anti-infectives are antibiotics, including penicillin, tetracycline, chloramphenicol, sulfacetamide, sulfamethazine, sulfadiazine, sulfamerazine, sulfamethizole and/or sulfisoxazole; antiviral agents; antibacterial agents such as erythromycin and/or clarithromycin, and/or other anti-infectives including nitrofurazone and the like.

In an embodiment, the dermatological agents are vitamin A and/or vitamin E.

In an embodiment, the medication for the treatment of nausea and/or sickness is chlorpromazine, granisetron, perphenazine, prochlorperazine, promethazine, thiethylperazine, triflupromazine and/or trimeprazine;

In an embodiment, the progestogens are progesterone, 19-norprogesterone, norethindrone, norethindrone acetate, chlormadinone, ethisterone, etonogestrel, medroxyprogesterone acetate, hydroxyprogesterone caproate, norethynodrel, norelgestromin, 17.alpha.-hydroxyprogesterone, dydrogesterone, dimethisterone, ethinylestrenol, norgestrel, demegestone, promegestone and/or megestrolacetate.

in an embodiment, the small molecules are an anti-inflammatory agent selected from the group consisting of: acemetacin, acetamidocaproic acid, bendazac, benoxaprofen, bermoprofen, bucloxic acid, butibufen, cinmetacin, clidanac, clopirac, felbinac, fenbufen, fenclozic acid, fenoprofen, fentiazac, flunoxaprofen, flurbiprofen, ibuprofen, indomethacin, isofezolac, isoxepac, ketoprofen, lonazolac, loxoprofen, metiazinic acid, mofezolac, naproxen, oxaprozin, pirazolac, pirprofen, pranoprofen, protizinic acid, sulindac, suprofen, suxibuzone, tiaprofenic acid, tolmetin, and/or tropesin. bermoprofen, bucloxic acid, isoxepac, ketoprofen, loxoprofen, zaltoprofen, ampiroxicam, bucolome, celecoxib, difenpiramide, mofebutazone, nimesulide, paranyline, parecoxib, parsalmide, piketoprofen, talniflumate, tenidap, terofenamate, valdecoxib, 21-acetoxypregnenolone, alclometasone, betamethasone, alfa-bisabolol, budesonide, clobetasone, cyclosporin, deflazacort, dexamethasone, diflorasone, desonide, desoximetasone, diflorasone, diflucortolone, difluprednate, ditazol, everolimus, fluazacort, fludrocortisone, flumethasone, fluocinolone, fluocinonide, fluocortin butyl, fluocortolone, fluprednidene acetate, glucametacin, halcinonide, halobetasol propionate, halometasone, halopredone acetate, hydrocortisone, ibuproxam, loteprednol etabonate, mazipredone, memetasone, methylprednisolone, mometasone furoate, oxyphenbutazone, perisoxal, pimecrolimus, prednisolone, prednisone, rimexolone, sirolimus, triamcinolone and/or tacrolimus.

In an embodiment, the small molecule is ibuprofen and/or diclofenac.

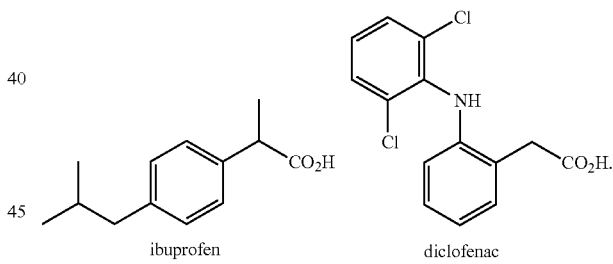

ibuprofen                diclofenac

In an embodiment, the small molecule is a wound healing compound. In an embodiment, the wound healing compound is bosentan. In an embodiment, the small molecule is an antibiotic. In an embodiment, the antibiotic is vancomycin.

In an embodiment, the protein is cytokine or peptide. In an embodiment, the peptide of the pharmaceutical composition has 2-900 amino acids.

In an embodiment, the amino acid, peptide or protein has a molecular weight of 50 Daltons to 300,000 Daltons. In some embodiments, the therapeutic compound is a carbohydrate or nucleic acid molecule having a molecular weight between 50-5M Daltons.

In an embodiment, the peptides are polypeptides such as insulin, cytokine, vaccine antigen, growth hormone releasing factor, or antibody. In an embodiment, the polypeptide has a molecular weight of 1000 Daltons to 300,000 Daltons.

As described above, the pharmaceutical compositions described herein, at times referred to as lipid vesicles or lipid compositions or formulations, can be used to deliver a therapeutic compound, including but not limited to small molecules, peptides, proteins, carbohydrates, nucleic acids, vaccine antigens, and/or plant extracts. The lipid vesicle formulations include one or more lipid (e.g., phospholipid) bilayers that contain an oil-in-water emulsion. The oil-in-water emulsion includes droplets that are generally less than 1 μm within the aqueous interior of the lipid vesicles, which are generally multilamellar, having multiple lipid bilayers. The biphasic lipid vesicle formulations may also include one or more other lipid vesicle components including but limited to fatty substances such as cholesterol, penetration enhancers, surfactants, solvents etc. to adapt the lipid vesicle formulations to suit physicochemical properties related to the target skin. The therapeutic compound, penetration enhancers, surfactants and/or other lipid vesicle components can be incorporated into the lipid bilayer and/or within the oil-in-water emulsion.

In an embodiment, the lipid vesicles can be formulated to have compounds, penetration enhancing agents, surfactants and/or other lipid vesicle component selectively incorporated into the lipid bilayers and/or the oil-in-water emulsion at different stages of production. Thus, a substantial degree of control can be maintained over the location within the lipid vesicles at which the compound, penetration enhancing agents, and/or other lipid vesicle component. are incorporated. The compound, for example, can be added only to the components of the oil-in-water emulsion, only to the components of the lipid bilayers, or to both the oil-in-water emulsion and the lipid bilayers during production of the lipid vesicles.

The structure and composition of these lipid vesicle formulations can be tuned to allow the one or more compound, s to deeply penetrate the skin. The lipid bilayers and oil-in-water emulsion of the lipid vesicle formulations sequester the one or more compounds and other pharmaceutical excipients to provide enhanced stability and sustained release of the compounds. In an embodiment, the biphasic lipid vesicle formulations optionally further comprises one or more other lipid vesicle components including but limited to fatty substances such as cholesterol, penetration enhancers, surfactants, and solvents, and combinations thereof.

In an embodiment, the lipid bilayer of the lipid vesicle further comprises a fatty substance to, for example, enhance the strength of the lipid bilayer. In an embodiment, the fatty substance is cholesterol, cholesterol derivatives, coprostanol, cholestanol, cholestane, or long chain fatty acids or combinations thereof. In an embodiment, the lipid bilayer of the lipid vesicle composition further comprises 0.1 wt % to 10 wt % cholesterol and/or a cholesterol derivative. In some embodiments, the lipid bilayer comprises from 1 wt % to 5 wt % cholesterol and/or a cholesterol derivative.

The lipid bilayer of the lipid vesicle composition may include 0.1 wt % to 5 wt % cholesterol or a derivative thereof. In some embodiments, the lipid bilayer of the lipid vesicle composition comprises 0.1 wt % to 3 wt % cholesterol or a derivative thereof. In some embodiments, the lipid bilayer comprises 2 wt % cholesterol or a derivative thereof.

In an embodiment, the lipid bilayer of the lipid vesicle composition optionally further comprises one or more penetration enhancers in addition to the one or more penetration enhancing agents. The skin penetration enhancers includes any known skin penetration enhancers not including the one or more penetration enhancing agents such as those described by Adrian C. Williams and Brian W. Barry Advanced Drug Delivery Reviews 64 (2012) 128-137; or by Majella E. Lane Int. J. Pharm. 447 (2013) 12-21.

It would be appreciated that the one or more additional penetration enhancers in addition to the penetration enhancing agents described herein can be added to the formulations.

In some embodiments, the skin penetration enhancer is selected from one or more of an alcohol such as ethanol or isopropyl alcohol; an amide such as azone; an ester such as ethyl acetate, padimate 0, ethyl oleate, glyceryl monoleate, glyceryl monocaprate, glyceryl tricaprylate, isopropyl myristate, isopropyl palmitate, propylene glycol monolaurate, or propylene glycol monocaprylate; an ether alcohol such as Transcutol® (e.g., Transcutol P, 2-(2-ethoxyethoxy) ethanol); a fatty acid such as lauric acid, linoleic acid, linolenic acid, myristic acid, oleic acid, palmitic acid, stearic acid, or isostearic acid; a glycol such as dipropylene glycol, propylene glycol, 1,2-butylene glycol, or 1,3-butylene glycol; a pyrrolidone such as N-methyl-2-pyrrolidone or 2-pyrrolidone; a sulphoxide such as decylmethyl sulphoxide or dimethyl sulphoxide.

In an embodiment, the one or more penetration enhancers are fatty acylated amino acids such as monolauroyllysine and/or dipalmitoyllysine.

In an embodiment, the lipid bilayer optionally further comprises a hydrophilic solvent to, for example, solubilize the vesicle forming lipids. In an embodiment, the hydrophilic solvents include but are not limited to propylene glycol, glycerol, polyethylene glycol having a molecular weight ranging between 300 and 8000, ethanol, and combinations thereof.

In an embodiment, the oil-in-water emulsion comprises an aqueous medium having water and, optionally, one or more lipophilic additives, such as preservatives (parabens, phenoxy ethanols, benzalkonium salts, etc.), antioxidants (ascorbic acid, ascorbyl palmitate, BHA, BHT, a-tocopherol), waxes and viscosity enhancing agents (long chain fatty alcohols and their esters, fatty acids, beeswax, olive oil, glyceryl stearate, cetyl alcohol, stearyl alcohol, myristyl myristate, and cetyl palmitate, stearyl heptanoate, and/or stearyl palmitate.

In an embodiment, the oil-in-water emulsion includes 0.1 wt % to 25 wt % of the one or more lipophilic additives.

The Applicant has also shown that penetration enhancing agents such as polycationic surfactants enhance skin penetration of the compound relative to otherwise same or similar composition except with a monocationic surfactant in place of the polycationic surfactants.

Accordingly, the present application further includes a biphasic lipid vesicle composition comprising:
  a) lipid vesicles comprising a lipid bilayer comprising vesicle forming lipids,
  b) an oil-in-water emulsion entrapped in the biphasic lipid vesicles, and comprising one or more polycationic surfactants; and
  c) one or more compounds entrapped in the lipid bilayer and/or the oil-in-water emulsion.

In an embodiment, the biphasic lipid vesicle composition is a cosmetic composition. In an embodiment, the biphasic lipid vesicle composition is a pharmaceutical composition.

In an embodiment, the biphasic lipid vesicle composition is for the topical delivery of the one or more compounds. In an embodiment, the topical delivery is for intradermal, transdermal and/or transmucosal delivery.

In an embodiment, the biphasic lipid vesicle composition comprises a suspension of the biphasic lipid vesicles.

In an embodiment, the polycationic surfactants are one or more gemini surfactants.

A gemini surfactant is a surfactant molecule which contains more than one hydrophobic tail. Each hydrophobic tail has a hydrophilic head (Menger and Keiper, 2000; Kirby et al., 2003). The hydrophobic tails or hydrophilic heads are linked together by a spacer. The hydrophobic tails can be identical or differ. Likewise, the hydrophilic heads can be identical or differ. Further, the hydrophilic heads may be anionic (e.g. of a phosphate, sulphate or carboxylate type), cationic (e.g. of a quaternary ammonium type), or neutral (e.g. of a polyether, peptide or sugar type) (Menger and Keiper, 2000). In aqueous solutions, gemini surfactants spontaneously aggregate into micelles whose shape and size are particularly sensitive to the length and hydrophobic or hydrophilic nature of the spacer. The spacer can be variable, namely short (e.g., 2 methylene groups) or long (e.g., more than 12 methylene groups); rigid (e.g., stilbene) or flexible (e.g., methylene chain); and polar (e.g., polyether, ethoxyl or polyethoxyl) or nonpolar (e.g., aliphatic, aromatic) (Menger and Keiper, 2000). As the hydrophobic tails, hydrophilic heads and spacer can vary with regard to the above aspects, innumerable different molecules can be designed.

In an embodiment, the type of hydrophobic tail is a $C_3$-$C_{30}$ alkyl group, linear or branched, saturated or unsaturated. In an embodiment, the hydrophilic heads may be anionic, cationic or neutral. In an embodiment, the hydrophilic heads are cationic.

In an embodiment, the polycationic surfactants are one or more gemini dicationic surfactants.

In an embodiment, the gemini surfactants comprise a linear hydrocarbon tailgroups and quaternary ammonium headgroups. The general structure of one type of gemini cationic surfactant includes a head group composed of two positively charged nitrogen atoms, separated by a spacer (n) of 3, 4, 6, 8, 10, 12, or 16 carbon atoms and each containing two methyl groups, and the tails consist of two saturated 12 or 16 carbon atom chains (m=10 or 14), respectively.

In an embodiment, the one or more gemini dicationic surfactants are of a quaternary ammonium type. In an embodiment, the one or more gemini dicationic surfactants are selected from the group consisting of 12-7NH-12, 12-7NCH$_3$-12, 16-3-16, 12-4(OH)$_2$-12, and 12-EO1-12. In an embodiment, the one or more gemini cationic surfactants are selected from the group consisting of 12-7NH-12, 12-7NCH$_3$-12, and 16-3-16.

In an embodiment, the one or more polycationic surfactants are polycationic amino acids. In an embodiment, the polycationic amino acids are selected from polylysine, polyarginine and combinations thereof.

In an embodiment, the oil-in-water emulsion of the biphasic lipid vesicles comprises from about 0.01 to about 5%, 0.05 to about 5%, 0.1% to about 5%, about 1% to about 5%, or about 2% to about 5% of the one or more polycationic surfactants. In an embodiment, the oil-in-water emulsion of the biphasic lipid vesicles comprises from about 0.01 to about 5% of the one or more polycationic surfactants.

In an embodiment, the oil-in-water emulsion of the biphasic lipid vesicles optionally comprises one or more additional surfactants (not including the polycationic surfactants). In an embodiment, the one or more additional surfactants are the one or more additional stabilizing surfactants as described above. In an embodiment, the oil-in-water emulsion of the biphasic lipid vesicles comprises from 0.1% to about 10% of the one or more surfactants. In an embodiment, the oil-in-water emulsion of the biphasic lipid vesicles comprises from about 0.01 to about 10%, 0.05 to about 10%, 0.1% to about 10%, about 1% to about 10%, about 2% to about 10%, 0.01 to about 7%, 0.05 to about 7%, 0.1% to about 7%, about 1% to about 7%, about 2% to about 7%, of the one or more surfactants.

When used with one or more additional surfactants, the oil-in-water emulsion of the biphasic lipid vesicles comprises from about 0.1% to about 10% of the one or more polycationic surfactants. In an embodiment, the oil-in-water emulsion of the biphasic lipid vesicles comprises from about 0.01 to about 10%, 0.05 to about 10%, 0.1% to about 10%, about 1% to about 10%, about 2% to about 10%, 0.01 to about 7%, 0.05 to about 7%, 0.1% to about 7%, about 1% to about 7%, about 2% to about 7%, of the one or more polycationic surfactants.

In an embodiment, the biphasic lipid vesicle composition further includes one or more penetration enhancing agents wherein the one or more penetration enhancing agents are one or more non-ionic surfactants having a HLB of about 10 or less alone, or in combination with one or more penetration enhancing agents selected from one or more terpenes, alkaloids, salicylate derivatives, and polycationic surfactants and combinations thereof as described above.

In an embodiment, the wt % water and oil in the oil-in-water emulsion is as described above.

In an embodiment, the vesicle forming lipids are as described above.

In an embodiment, the one or more one or more compounds are entrapped in oil-in-water emulsion of the biphasic lipid vesicle, the lipid bilayer.

In an embodiment, the one or more compounds are entrapped in the lipid bilayer, the oil-in-water emulsion of the biphasic lipid vesicle or both as described above.

In an embodiment, amount of one or more compound in the lipid bilayer, and the oil-in-water emulsion is as described above.

In an embodiment, the one or more compounds are selected from but not limited to, small molecules including negatively charged small molecules, carbohydrates, nucleic acids such as RNA or DNA or hybrids thereof, plasmid DNA, oligonucleotides, including synthetic oligonucleotides, viral DNA, DNA vaccines, and the like, protein, peptides including peptide antigens such as vaccines antigens, immunoglobulins, immunomodulators, hormones, toxins, and/or enzymes, as well as plant extracts, and/or vitamins.

In an embodiment, the one or more compounds are selected from but not limited to peptides, carbohydrates, nucleic acids, vaccine antigens, plasmid DNA, DNA vaccines, peptide vaccines, immunoglobulins, immunomodulators, oligonucleotides, hormones, toxins, and enzymes. In an embodiment, the one or more compounds are selected from the nucleic acids, plasmid DNA, DNA vaccines, and/or oligonucleotides. In an embodiment, the one or more compounds are selected from the nucleic acids, plasmid DNA, DNA vaccines, and/or oligonucleotides.

In an embodiment, the biphasic lipid vesicle compositions optionally further comprise one or more other lipid vesicle components including but limited to fatty substances such as cholesterol, penetration enhancers, surfactants, and/or solvents, and combinations thereof as described above.

In an embodiment, the biphasic lipid vesicle compositions of the disclosures are for the topical delivery of the one or more compounds. In an embodiment, the topical delivery is for intradermal, transdermal or transmucosal delivery.

As noted above, in an embodiment, the biphasic lipid vesicle compositions of the disclosure described herein can be cosmetic compositions.

In an embodiment, the biphasic lipid vesicle cosmetic compositions of the disclosure suitably optionally comprise components generally used in cosmetic products, for example, moisturizers, antioxidants, oily components, UV absorbers, emulsifiers, thickeners, alcohols, powder components, colorants, aqueous components, water, and/or various skin nutrients, etc., as needed, within the range that does not impair the effect of the present compositions and system. The cosmetic composition may contain conventional adjuvants and carriers, such as antioxidants, stabilizers, solubilizers, vitamins, pigments, and/or fragrances.

In an embodiment, the biphasic lipid vesicle compositions of the disclosure described herein can be formulated as a cream, tonic, ointment, paste, lotion, gel, oil, liquid spray, foundation or powder.

In an embodiment, ointments or creams can be formulated with an aqueous or oily base with the addition of suitable thickening and/or gelling agents. Such bases may include water and/or an oil such as liquid paraffin or a vegetable oil such as peanut oil or castor oil. An exemplary base is water. Thickening agents which can be used according to the nature of the base include aluminum stearate, hydrogenated lanolin, and the like. Further, lotions can be formulated with an aqueous base and will, in general, include one or more of the following: stabilizing agents, emulsifying agents, dispersing agents, suspending agents, thickening agents, coloring agents, perfumes, and the like. Ointments and creams can also contain excipients, such as starch, tragacanth, cellulose derivatives, carbopols, polyethylene glycols, silicones, bentonites, Veegum (magnesium aluminium silicate), silicic acid, and talc, or mixtures thereof. Lotions may be formulated with an aqueous or oily base and will, in general, also include one or more of the following: stabilizing agents, emulsifying agents, dispersing agents, suspending agents, thickening agents, coloring agents, perfumes, and the like. Foams may be formed with known foaming or surface active agents.

In an embodiment, the gels may be formed by mixing the delivery system (e.g. the biphasic vesicles described herein) with gelling agents such as collagen, pectin, gelatin, agarose, chitin, chitosan and alginate. The delivery system may be incorporated into liquids, formulated as topical solutions, aerosols, mists, sprays, drops and instillation solutions for body cavities. Administration of the delivery system to for example the mucosal membrane may be performed by aerosol, which can be generated by a topical aerosol spray pump or actuator, or by instillation.

Also provided is a container comprising a composition described herein. The container is optionally a spray container optionally an aerosol spray pump container.

In an embodiment, the biphasic lipid vesicle compositions of the disclosure described herein is comprised in a coated substrate such as dressings, packings, films or meshes which can coated with the biphasic lipid vesicle composition and used directly on the skin or mucosal membrane.

In an embodiment, the biphasic lipid vesicle compositions of the disclosure described herein may be comprised in a transdermal delivery system taking one of various forms, for example, a patch or a mask sheet.

In an embodiment, the transdermal delivery system comprises
   a backing layer; and
   a matrix layer comprising a biphasic lipid vesicle composition described herein, disposed on the backing layer,
   wherein the matrix layer is configured for contacting skin.

In an embodiment, the backing layer is or comprises a polymer selected from the group consisting of polyesters, such as polyethylene terephthalates (PET), as well as polycarbonates, polyolefins such as, for example, polyethylenes, polypropylenes or polybutylenes, polyethylene oxides, polyurethanes, polystyrenes, polyamides, polyimides, polyvinyl acetates, polyvinyl chlorides, polyvinylidene chlorides, copolymerisates such as, for example, acrylonitrile-butadiene-styrene terpolymers, or ethylene-vinyl acetate-copolymerisates. A preferred material for a backing layer is selected from a polyester, particular preferably from a polyethylene terephthalate. A backing layer of this type may, for example, be obtained from 3M (USA) under the trade name Scotchpak 1109.

In an embodiment, the backing layer is an occlusive backing layer,

The backing layer can for example be produced from polyesters.

In another embodiment, the backing layer comprises an overtape which protrudes laterally beyond the edges of the matrix layer, permitting adhesion or better adhesion of the transdermal delivery system to the skin. The overtape can comprise a layer of adhesive, free from active ingredient and overtape film. The overtape film can be a polymer selected from the group formed by polyolefins, olefin copolymerisates, polyesters, copolyesters, polyamides, copolyamides, polyurethanes and the like. Examples of suitable materials that may be cited are polyesters, and of these, polyethylene terephthalates in particular, as well as polycarbonates, polyolefins such as, for example, polyethylenes, polypropylenes or polybutylenes, polyethylene oxides, polyurethanes, polystyrenes, polyamides, polyimides, polyvinyl acetates, polyvinyl chlorides, polyvinylidene chlorides, copolymerisates such as, for example, acrylonitrile-butadiene-styrene terpolymers, or ethylene-vinyl acetate-copolymerisates.

In an embodiment, the adhesive can for example be polyisobutylene (PIB) adhesive.

In an embodiment, the backing layer has a thickness which is at least about 5 µm, at least about 10 µm, at least about 15 µm, at least about 20 µm, at least about 25 µm, at least about 50 µm, at least about 75 µm, at least about 100 µm, at least about 125 µm, or up to approximately 250 µm, up to approximately 200 µm, up to approximately 150 µm, up to approximately 100 µm or up to 50 µm, or any combination of the foregoing. The backing layer can for example have a thickness including or between 5 µm and 200 µm or any 0.1 µm increment between 5 µm and 200 µm.

When the transdermal delivery system is a patch, the backing layer thickness may be at least about 75 µm or at least about 100 µm and less than for example 200 µm or less than for example 150 µm When the transdermal delivery system is a mask, the backing later thickness may be at least 10 µm or at least 20 µm and less than for example 100 µm or less than for example 75 µm.

The matrix layer has a surface which is intended to be placed on the skin can be referred to as the application side. The application side may be configured so as to comprise a pressure-sensitive adhesive over its entire surface, for example a surface self-adhesive glue or it may be configured so as to be adhesive over only a portion of its surface.

In an embodiment, the transdermal delivery system further comprises a protective layer, also known as a release liner, which is applied to the composition comprising matrix layer and which is removed prior to application of the transdermal delivery system. to facilitate removal of the protective layer, in some embodiments, the protective layer protrudes beyond the edge of the backing layer e.g. the remaining patch.

In an embodiment, the transdermal delivery system is a patch.

In an embodiment, the one or more compounds are therapeutic compounds. Therefore, the biphasic lipid vesicle compositions of the disclosure described herein are pharmaceutical compositions. Accordingly, the biphasic lipid vesicles of the disclosure are suitably formulated into pharmaceutical compositions for administration to subjects in a biologically compatible form suitable for topical administration comprising pharmaceutical acceptable carriers. In an embodiment, the one or more compounds are therapeutic compounds are selected from the one or more therapeutic compounds described herein.

III. Methods of Preparing the Compositions of the Disclosure

The compositions of the disclosure as described above are prepared by mixing oil components of the oil-in-water emulsion with aqueous components of the oil-in-water emulsion wherein either the oil components or aqueous components of the oil-in-water emulsion comprises one or more surfactants for emulsification of the oil component with the aqueous component of the oil-in-water emulsion. In an embodiment, the surfactant is mixed with the aqueous component and added to the oil for formation of an emulsion. The oil-in-water emulsion is then mixed with the solubilized vesicle-forming lipid and, if added, other lipid components under mixing conditions effective to form the biphasic lipid vesicles.

The one or more penetration enhancing agents and the one or more compounds are added to oil component of the oil-in-water emulsion, to the aqueous component of the oil-in-water emulsion or both. Alternatively, or in addition to, the one or more penetration enhancing agents and the one or more compounds can be added to the lipid component.

Accordingly, the present application includes a method of preparing biphasic lipid vesicles comprising:
a) preparing an oil-in-water emulsion comprising one or more surfactants, by mixing oil components of the oil-in-water emulsion with aqueous components of the oil-in-water emulsion, wherein the oil components and/or the aqueous components of the oil-in-water emulsion comprises the one or more surfactants;
b) solubilizing vesicle forming lipids in an acceptable solvent other than water;
c) adding one or more compounds and one or more penetration enhancing agents to the oil components and/or the aqueous components of step a), and/or the solubilized vesicle forming lipids of step b);
d) adding the oil-in-water emulsion to the solubilized vesicle forming lipids; and
e) mixing the oil-in-water emulsion and the solubilized vesicle forming lipids under mixing conditions effective to form the biphasic lipid vesicles comprising a lipid bilayer comprising vesicle forming lipids, and an oil-in-water emulsion entrapped in the biphasic lipid vesicles.

In an embodiment, a pharmaceutical composition, i.e., lipid vesicle composition, is provided for the topical administration of a compound, wherein the composition comprises a lipid vesicle comprising an exterior lipid bilayer, an oil-in-water emulsion and the therapeutic compound, the composition being formed by: (a) mixing oil with water to form the oil-in-water emulsion; (b) mixing the oil-in-water emulsion of (a) with at least one vesicle forming lipid such that the oil-in-water emulsion is coated by the exterior lipid bilayer; and (c) adding the therapeutic compound and penetration enhancers during (a) and/or (b); wherein the compound is a molecule having a molecular weight between 50-5M Daltons; and the one or more penetration enhancing agents increases a quantity of the compound that absorbs into a quantity of skin relative to the same composition in the absence of the one or more penetration enhancing agents.

In an embodiment, the mixing oil components of the oil-in-water emulsion with aqueous components of the oil-in-water emulsion vesicles of step a) and/or the mixing conditions of step e) comprises using agitation such as homogenization or emulsification, or micro-emulsion techniques which do not involve agitation. In an embodiment, the mixing comprises high pressure homogenizing. The high pressure homogenizing provides relatively precise control over the composition of the lipid vesicles. High pressure homogenizing is suitable for small molecules and peptides or proteins that are resistant to shearing. In an embodiment, the composition that is formed is any one of the lipid vesicle compositions described herein.

In an embodiment, other lipid components are added to any one of steps a) to e).

In an embodiment, the one or more surfactants are selected from one or more stabilizing surfactants and/or one or more polycationic surfactants described herein.

In an embodiment, the one or more penetration enhancing agents, the one or more compounds, the oil-in-water emulsion, the vesicle forming lipid, the acceptable solvent and/or the other lipid components are as described above.

The lipid vesicle compositions of the disclosure can also be prepared by methods known in the art, for example by the methods disclosed in U.S. Pat. Nos. 5,993,852, 5,853,755 and 5,993,851 incorporated herein by reference.

In an embodiment, the biphasic lipid vesicle compositions of the disclosure described herein may be comprised in a transdermal delivery system taking one of various forms, for example, a patch or a mask sheet. In an embodiment, the biphasic lipid vesicle compositions is a transdermal patch.

In an embodiment, a transdermal patch can be prepared using procedures known in the transdermal patch art. The process for preparation will generally involve formulating the matrix layer comprising the biphasic (i.e., mixing the adhesive and the biphasic lipid vesicles and additives, if any), casting the matrix layer onto the backing or release liner layer, and removing solvent from the matrix

IV. Methods and Uses of the Disclosure

The biphasic lipid vesicles are liposomes i.e., microscopic vesicles composed of a single phospholipid bilayer or a plurality of concentric phospholipid bilayers which enclose the oil-in-water emulsion. These lipid vesicles serve as compound carriers for the topical delivery of compound that may be hydrophobic or hydrophilic. The lipid vesicles are generally biocompatible, biodegradable and non-toxic vehicles for drug delivery.

The compositions of the disclosures can be used for the topical delivery of one or more compounds. Accordingly, the present application includes a method of delivering one or more compounds by administering the biphasic lipid vesicle compositions of the disclosures topically to the skin or mucosal membrane to a subject.

The application also includes a use of the lipid vesicle compositions of the disclosures of the disclosure for delivering one or more compounds topically to the skin or mucosal membrane, as well as a use of the lipid vesicle compositions of the disclosures of the disclosure for the preparation of a medicament for delivering one or more compounds topically to the skin or mucosal membrane. The application further includes the lipid vesicle compositions of the disclosures of the disclosure for delivering one or more compounds topically to the skin or mucosal membrane.

The biphasic lipid vesicle compositions of the disclosure comprising the one or more penetration enhancing agents described herein have been shown to improve the skin permeation of the one or more compounds relative to otherwise same or similar compositions except in the absence of the one or more penetration enhancing agents. The biphasic lipid vesicle compositions of the disclosure and the biphasic lipid vesicle cosmetic compositions of the disclosure comprising the one or more polycationic surfactants described herein have been shown to improve the skin permeation of the one or more compounds relative to otherwise same or similar compositions except with a monocationic surfactant in place of the di- or polycationic surfactant.

Accordingly, the present application also includes a method of improving topical delivery of one or more compounds comprising administering an effective amount of the biphasic lipid vesicle compositions of the disclosures of the disclosure to the skin or mucosal membrane of a subject in need thereof.

The application also includes a use of the lipid vesicle compositions of the disclosure or the lipid vesicle cosmetic compositions of the disclosure for improving topical delivery of one or more compounds to the skin or mucosal membrane, as well as a use of the lipid vesicle compositions of the disclosure or the lipid vesicle cosmetic compositions of the disclosure for the preparation of a medicament for improving topical delivery of one or more compounds to the skin or mucosal membrane. The application further includes the lipid vesicle compositions of the disclosure or the lipid vesicle cosmetic compositions of the disclosure for improving topical delivery of one or more compounds to the skin or mucosal membrane.

In an embodiment, the present application includes a method of treating or preventing skin conditions related to excessive or defective collagen production in a subject comprising administering to the subject in need thereof, an effective amount of the lipid vesicle cosmetic compositions of the disclosure to a subject in need thereof.

The application also includes a use of the lipid vesicle cosmetic compositions of the disclosure for treating or preventing s preventing skin conditions related to excessive or defective collagen, as well as a use of the lipid vesicle cosmetic compositions of the disclosure for the preparation of a medicament for treating or preventing skin conditions related to excessive or defective collagen. The application further includes the lipid vesicle cosmetic compositions of the disclosure for treating or preventing skin conditions related to excessive or defective collagen.

In an embodiment, the skin conditions related to excessive or defective collagen is skin aging, skin elasticity, striae, stretchmarks, wrinkles, collagen vascular diseases such as cutaneous scleroderma, morphoea, lupus, rheumatoid arthritis, temporal arteritis, fereditary collagen diseases such as Ehlers-Danlos syndrome, Marfan's syndrome.

In an embodiment, the one or more compound are one or more therapeutic compounds. Therefore, the biphasic lipid vesicle compositions is a biphasic lipid vesicle pharmaceutical composition.

Accordingly, the present application also includes a method of treating disease, disorder or condition treatable by delivering one or more therapeutic compounds by administering a therapeutically effective amount of the biphasic lipid vesicle pharmaceutical compositions of the disclosure topically to the skin or mucosal membrane to a subject in need thereof. In an embodiment, the biphasic lipid vesicle compositions of the disclosure are administered topically to the skin.

The application also includes a use of lipid vesicle compositions of the disclosure for treating diseases, disorders or conditions treatable by delivering one or more therapeutic compounds of the disclosure topically to the skin or mucosal membrane as well as a use of lipid vesicle compositions of the disclosure for the preparation of a medicament for treating diseases, disorders or conditions treatable by delivering one or more therapeutic compounds topically to the skin or mucosal membrane to a subject in need thereof. The application further includes lipid vesicle compositions the application for treating diseases, disorders or conditions treatable by delivering one or more therapeutic compounds topically to the skin or mucosal membrane.

In an embodiment, the disease, disorder or condition treatable by delivering one or more therapeutic compounds by administering a therapeutically effective amount of the biphasic lipid vesicle pharmaceutical compositions of the disclosure topically to the skin or mucosal membrane is skin condition related to excessive or defective collagen production, inflammation, pain, a fungal infection, a viral infection, skin/dermatological conditions, rheumatic conditions, joint conditions, skin aging or cancer. In an embodiment, the disease, disorder or condition is skin aging. In an embodiment, the disease, disorder or condition is skin condition related to excessive or defective collagen production.

In an embodiment, the disease, disorder or condition is a skin condition. In an embodiment, the skin condition is scleroderma, atopic dermatitis, psoriasis, conditions characterized by any cytokine deficiency, conditions characterized by IFNγ deficiency, genodermatoses (skin diseases of genetic origin) including epidermal fragility disorders, keratinization disorders, hair disorders, pigmentation disorders, porphyrias, multisystem disorders and cancer disorders. In an embodiment, the disease, disorder or condition is forms of inherited epidermolysis bullosa (such as junctional EB and dystrophic EB), lamellar ichthyosis and/or X-linked ichthyosis and xeroderma pigmentosum.

In an embodiment, the disease, disorder or condition is an infection. In an embodiment, the infection is a viral infection, a bacterial infection or fungal infection.

In an embodiment, the disease, disorder or condition is sexual dysfunction. In an embodiment, the sexual dysfunction is erectile dysfunction or impotence.

In an embodiment, the disease, disorder or condition is genetic warts.

In an embodiment, the disease, disorder or condition is pain or inflammation. In an embodiment, the pain is acute pain or chronic pain.

In an embodiment, the subject is a mammal. In an embodiment, the subject is a human.

The dosage of compositions of the disclosure can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. Compositions of the disclosure may be administered initially in a suitable dosage that may be adjusted as required, depending on the clinical response. Dosages will generally be selected to maintain a serum level of compounds of the disclosure from about 0.01 µg/mL to about 1000 µg/mL, or about 0.1 µg/mL to about 100 µg/mL. As representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. Compounds of the disclosure may be administered in a single daily, weekly or monthly dose or the total daily dose may be divided into two, three or four daily doses.

In an embodiment, the compositions of the disclosure are administered at least once a week. However, in another embodiment, the compounds are administered to the subject from about one time per two weeks, three weeks or one month. In another embodiment, the compounds are administered about one time per week to about once daily. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compounds of the disclosure, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration is required. For example, the compounds are administered to the subject in an amount and for duration sufficient to treat the subject.

EXAMPLES

The following non-limiting examples are illustrative of the present application.

Example 1: Exemplary Lipid Vesicle Compositions

A. Methods
Method 1: In Vitro Diffusion Cell Studies:

Full thickness human breast skin was obtained from female donors undergoing elective mammoplasty surgeries at the Royal University Hospital, University of Saskatchewan (Saskatoon, SK, Canada). Approval for skin collection was granted by the Human Ethics Committee at the University of Saskatchewan. The skin was collected within 2 h following surgery, trimmed of subcutaneous fat, and stored at −20° C. until use. In-line Bronaugh Flow-through diffusion cells with a 9 mm orifice diameter (0.63 cm$^2$) were mounted on a water insulated cell warmer (PermeGear, Inc., Hellertown, PA) and set to a constant temperature of 32° C. Precut 1 cm$^2$ skin sections were placed in the diffusion cells with the stratum corneum side facing up. Perfusion buffer (100 mM phosphate buffer with 0.05% Na-azide) at 37° C. was circulated through the lower half of the diffusion cells at a rate of 1 mL/h using a peristaltic pump. The surface of the skin was dosed with 0.1 mL of the formulations. Following 24 h incubation, the skin samples were removed from the cells and their surface was washed 3 times with 10 mL of water each time. Each skin sample was blot dried and tape-stripped twice using clear stationary tape to remove surface excess formulation. Skin samples were analyzed by UPLC of skin homogenates or by confocal microscopy of cryosections.

Method 2: Skin Homogenate Preparation for UPLC Analysis

Skin samples were individually homogenized using the gentleMACS™ Dissociator (Miltenyi Biotec, Inc., Auburn, CA). Each skin section was reconstituted in 1 mL of methanol (for diclofenac samples) or 1 mL acetonitrile (for ibuprofen samples), added to a gentleMACS™ M tube (Miltenyi Biotec, Inc.) and homogenized using the protein extraction program (10×55 sec). Samples were then filtered using a 0.2 µm Acrodisc® GH Polypro membrane syringe filter (Pall Corp., Ville St. Laurent, QC, Canada) into 2 mL LC/GC certified clear glass maximum recovery vials (Waters Corp., Milford, MA).

The ACQUITY H-class UPLC chromatographic system, consisting of a bioQuaternary Solvent Manager, autosampler (bioSample Manager-Flow Through Needle), variable wavelength UV-detector (photodiode array eλ) and Column Manager, controlled by the Empower 3 software (Waters Corp.), was used for the analysis and method validation for the purpose of this study.

Analyses were performed on a 1.7 µm BEH300 C18 50 mm×2.1 mm i.d. column (Waters Corp.) heated to 30° C. (for diclofenac runs) and to 35° C. (for ibuprofen runs) with an injection volume of 5 µL. The mobile phase (Solvent A—0.65 methanol: 0.35 milliQ water with pH adjusted to 2.5 using phosphoric acid for diclofenac analysis and 0.67 milliQ water: 0.34 acetonitrile for ibuprofen analysis) was pumped at 0.45 mL/min (for diclofenac analysis) and 0.55 mL/min (for ibuprofen analysis), in isocratic mode. The total run time was 5 min and 10 min for diclofenac and ibuprofen analysis, respectively. The mobile phase, standard and sample solutions were filtered through a 0.2 µm Acrodisc® GH Polypro membrane syringe filter (Pall Corp.) and used at room temperature. The UV detection range was set at 200-260 nm for diclofenac and the collected data was graphed at 254 nm. For ibuprofen, the UV detection range was 200-250 nm and the collected data was graphed at 220 nm. The calibration and quantitation (total peak area) were all calculated using the Empower 3 software.

Method 3: In Vivo Studies

The animal experiments were approved by the University of Waterloo Committee on Animal Care Protocol Review Committee. For in vivo delivery CD1 mice (Charles River) were used. All animals (including controls) were anesthetized with isoflurane and close-shaved a day prior to treatment. The shaved area was cleaned with distilled water using sterile gauze and dried. Naked plasmid DNA solution or plasmid DNA formulations (50 µL containing 25 µg tD-tomato red fluorescence protein (RFP) coding plasmid for each animal) were applied on the shaved area, and covered with parafilm/Opsite occlusive dressing which was held in place with a plastic tape for 24 hours. The treated area of the skin was excised 24 hours after treatment.

Method 4: Confocal Microscopy

Mouse or human skin samples were characterized using confocal microscopy using a Zeiss LSM 710 confocal microscope. All samples were embedded in OCT compound matrix and frozen for cryosectioning. Skin samples were cryosectioned with a Leica CM1850 cryostat into 10 µm sections. Confocal microscopy images of the skin sections were obtained using a Zeiss LSM 710 CLSM using HeNelaser (543 and 633 nm) lines for tdTomato (546/579) and Rhodamine (570/590), 488 nm laser for FITC insulin and FITC-IgG and either the Plan-Apochromat 20×/0.80 dry objective or the 63×/1.40 oil immersion objective. Optical zoom selection was applied in selected cases. Laser intensity, pinhole and gain settings were kept consistent between sample sets to enable comparison of relative fluorescence intensity measurements between different treatments. Images were captured and processed using the Zen 2009 software.

The 'no treatment' sample was used to confirm gain and pinhole settings to exclude noise and autofluorescence background for the subsequent treatment samples.

B: Exemplary Lipid Vesicle Formulation Compositions
1. Exemplary Ibuprofen Lipid Vesicle Formulations
Step 1: Preparation of System A (Oil in Water Emulsion):
System A for Exemplary Ibuprofen Lipid Vesicle Formulations IB1-IB-6 (the Oil-In-Water Sub-Micron Emulsion) is as Follows:

| Oil Phase | Olive oil | 5% |
|---|---|---|
|  | Benzalkonium chloride | 0.05% |
|  | Propylparaben | 0.05% |
|  | Glyceryl monostearate NE | 1% |
|  | Cetyl alcohol | 0.6% |
|  | Synchrowax BB4 (beeswax) | 0.28% |
| Aqueous Phase | Ceteth-10 | 1% |
|  | Tween 80 | 1% |
|  | Methylparaben | 0.15% |
|  | Milli-Q Water | Qs to 100 |

Step 2: Procedure Preparation of System A (Oil-In-Water Submicron Emulsion) Preparation (Applicable to all Formulations):
1. The oil phase and aqueous phase ingredients were weighed out in separate beakers.
2. Both beakers were heated to ~70° C. to completely melt and incorporate all components.
3. The water phase was added to the oil phase in one quick addition, while stirring vigorously with a spatula to form an o/w crude emulsion, effectively yielding a homogenous milky solution (~2 min) in the 70° C. water bath.
4. The formulation was batch processed using the LV1 Microfluidizer or Nano DeBee homogenizer with Z5 module three times at 20,000 psi.

Step 3: Preparation of Vesicles:
Exemplary Ibuprofen Formulation IB1:

| Lipid Phase | Phospholipon 90H | 10% |
|---|---|---|
|  | Cholesterol | 2% |
|  | Propylene glycol | 7% |
|  | Oleth-2 | 1% |
|  | Ibuprofen | 5% |
| Aqueous Phase | System A | Qs to 100 |

Procedure for vesicle formation (applicable to all formulations):
1. The lipid phase components were weighed into a 20 mL glass vial.
2. The vial was heated to ~70° C. in a water bath to completely melt and incorporate all components.
3. The water phase (System A) was added to the liquid phase in one quick addition.
4. The mixture was intermittently vortexed and heated for 5 sec/5secfor 8-10 cycles until a uniform creamy lotion formed.

The following exemplary lipid vesicles formulations were prepared using the process described above for Ibuprofen Formulation IB1.

b. Ibuprofen Formulation IB2

| Lipid Phase | Phospholipon 90H | 10% |
|---|---|---|
|  | Cholesterol | 2% |
|  | Propylene glycol | 7% |
|  | Oleth-2 | 1% |
|  | Ibuprofen | 5% |
| Aqueous Phase | Menthol | 1% |
|  | Camphor | 1% |
|  | System A | Qs to 100 |

Note: Menthol and camphor were premixed without heating, in a glass vial using a spatula to form a eutectic mixture. After the mixture was fully mixed and in a liquid state, System A was added and vortexed well. This mixture was then added to the lipid phase as above.

c) Exemplary Ibuprofen Formulation IB3A

| Lipid Phase | Phospholipon 90H | 10% |
|---|---|---|
|  | Cholesterol | 2% |
|  | Propylene glycol | 7% |
|  | Piperine | 0.1% |
|  | Oleth-2 | 1% |
|  | Ibuprofen | 5% |
| Aqueous Phase | System A | Qs to 100 | d) Exemplary Ibuprofen Formulation IB3B

| Lipid Phase | Phospholipon 90H | 10% |
|---|---|---|
|  | Cholesterol | 2% |
|  | Propylene glycol | 7% |
|  | Piperine | 0.1% |
|  | Oleth-2 | 2% |
|  | Ibuprofen | 5% |
| Aqueous Phase | System A | Qs to 100 | e) Exemplary Ibuprofen Formulation IB4A

| Lipid Phase | Phospholipon 90H | 10% |
|---|---|---|
|  | Cholesterol | 2% |
|  | Propylene glycol | 7% |
|  | Methyl salicylate | 2.5% |
|  | Oleth-2 | 1% |
|  | Ibuprofen | 5% |
| Aqueous Phase | System A | Qs to 100 | f) Exemplary Ibuprofen Formulation IB4B

| Lipid Phase | Phospholipon 90H | 10% |
|---|---|---|
|  | Cholesterol | 2% |
|  | Propylene glycol | 7% |
|  | Methyl salicylate | 2.5% |
|  | Oleth-2 | 2% |
|  | Ibuprofen | 5% |
| Aqueous Phase | System A | Qs to 100 | g) Exemplary Formulation IB5A

| Lipid Phase | Phospholipon 90H | 10% |
|---|---|---|
|  | Cholesterol | 2% |
|  | Propylene glycol | 7% |
|  | Nerol | 1% |
|  | Oleth-2 | 1% |
|  | Ibuprofen | 5% |
| Aqueous Phase | System A | Qs to 100 | h) Exemplary Ibuprofen Formulation IB5B

| Lipid Phase | Phospholipon 90H | 10% |
|---|---|---|
| | Cholesterol | 2% |
| | Propylene glycol | 7% |
| | Nerol | 1% |
| | Oleth-2 | 2% |
| | Ibuprofen | 5% |
| Aqueous Phase | System A | Qs to 100 | i) Exemplary Ibuprofen Formulation IB6A

| Lipid Phase | Phospholipon 90H | 10% |
|---|---|---|
| | Cholesterol | 2% |
| | Propylene glycol | 7% |
| | Thymol | 1% |
| | Oleth-2 | 1% |
| | Ibuprofen | 5% |
| Aqueous Phase | System A | Qs to 100 | j): Exemplary Ibuprofen Formulation IB6B

| Lipid Phase | Phospholipon 90H | 10% |
|---|---|---|
| | Cholesterol | 2% |
| | Propylene glycol | 7% |
| | Thymol | 1% |
| | Oleth-2 | 2% |
| | Ibuprofen | 5% |
| Aqueous Phase | System A | Qs to 100 |

2. Exemplary Diclofenac Lipid Vesicle Formulations

Step 1: Preparation of System A (Oil in Water Sub-Micron Emulsion)

System A for exemplary diclofenac lipid vesicle formulations DF1 and DF2 is as follows:

| Oil Phase | Olive oil | 5% |
|---|---|---|
| | Benzalkonium chloride | 0.05% |
| | Propyl paraben | 0.05% |
| | Crodamol GMS | 1% |
| | Cetyl alcohol | 0.6% |
| | Synchrowax BB4 | 0.28% |
| Aqueous Phase | Ceteth-10 | 1% |
| | Tween 80 | 1% |
| | Methyl paraben | 0.15% |
| | Milli-Q Water | Qs to 100 |

System A was prepared using the process described above for Ibuprofen Formulation IB1.

Step 2: Preparation of Vesicles

The following exemplary diclofenac lipid vesicles formulations were prepared using the process described above for Ibuprofen Formulation IB1.

a) Exemplary Diclofenac Formulation DF1

| Lipid Phase | Phospholipon 90H | 10% |
|---|---|---|
| | Cholesterol | 2% |
| | Propylene glycol | 7% |
| | Piperine | 1% |
| | Tween 80 | 1% |
| | PEG-4 dilaurate | 1% |
| | Diclofenac | 5% |
| Aqueous Phase | System A | Qs to 100 | b) Exemplary Diclofenac Formulation DF2

| Lipid Phase | Phospholipon 90H | 10% |
|---|---|---|
| | Cholesterol | 2% |
| | Propylene glycol | 7% |
| | Methyl Salicylate | 2.5% |
| | Tween 80 | 1% |
| | PEG-4 dilaurate | 1% |
| | Diclofenac | 5% |
| Aqueous Phase | System A | Qs to 100 |

3. Exemplary Peptide and Protein Lipid Vesicle Formulations

The following exemplary peptide and protein lipid vesicles formulations were prepared using the process described above for exemplary ibuprofen formulation IB1.

a) Exemplary 12 mer peptide (mwt 1200), insulin (mwt 6000) and IgG (150,000) lipid vesicle formulation 1 (Peptide lipid vesicle formulation 1)

Preparation of System A (Oil in Water Sub-Micron Emulsion) for Formulations:

| Oil Phase | Labrafac CC | 5% |
|---|---|---|
| | Glyceryl monostearate NE | 1.2% |
| | Cetyl alcohol | 0.6% |
| | Synchrowax BB4 (beeswax) | 0.3% |
| | Propylparaben | 0.05% |
| Aqueous Phase | Arlasilk EFA (Phospholipid EFA) | 5% |
| | Methylparaben | 0.15% |
| | Milli-Q Water | Qs to 100 |

Preparation of Vesicles:

| Lipid Phase | Phospholipid (Sunlipon 90H) | 7% |
|---|---|---|
| | Cholesterol | 1.75% |
| | Monolauroyl lysine | 2% |
| | Oleth-2 | 1% |
| | Propylene glycol | 7% |
| Aqueous Phase | Rhodamine-12mer peptide:12mer peptide 1:1 OR FITC insulin OR FITC-IgG | 0.1% |
| | System A | Qs to 100 | b) Exemplary 12 mer peptide (mwt 1200), insulin (mwt 6000) and IgG (150,000) lipid vesicle formulation 2 (Peptide lipid vesicle formulation 2)

Preparation of System A (Oil in Water Sub-Micron Emulsion):

| Oil Phase | Labrafac CC | 5% |
|---|---|---|
| | Glyceryl monostearate NE | 1.2% |
| | Cetyl alcohol | 0.6% |
| | Synchrowax BB4 (beeswax) | 0.3% |
| | Propylparaben | 0.05% |
| Aqueous Phase | Polysorbate 80 | 2% |
| | Sorbitan monopalmitate (Span 40) | 0.5 |
| | Methylparaben | 0.15% |
| | Milli-Q Water | Qs to 100 |

Preparation of vesicles:

| Lipid Phase | Phospholipid (Sunlipon 90H) | 7% |
|---|---|---|
| | Cholesterol | 1.75% |
| | PEG-4 dilaurate | 1% |
| | Propylene glycol | 7% | c) Exemplary 12 mer peptide (mwt 1200), insulin (mwt 6000) and IgG (150,000) lipid vesicle formulation 3 (Peptide lipid vesicle formulation 3)

Preparation of System A (Oil in Water Sub-Micron Emulsion):

| Oil Phase | Labrafac CC | 5% |
|---|---|---|
| | Glyceryl monostearate NE | 1.2% |
| | Cetyl alcohol | 0.6% |
| | Synchrowax BB4 (beeswax) | 0.3% |
| | Propylparaben | 0.05% |
| Aqueous Phase | Polysorbate 80 | 2% |
| | Sorbitan monopalmitate (Span 40) | 0.5 |
| | Methylparaben | 0.15% |
| | Milli-Q Water | Qs to 100 |

Preparation of Vesicles:

| Lipid Phase | Phospholipid (Sunlipon 90H) | 7% |
|---|---|---|
| | Cholesterol | 1.75% |
| | Monolauroyl lysine | 2% |
| | Oleth-2 | 1% |
| | Propylene glycol | 7% |
| Aqueous Phase | Rhodamine-12mer peptide:12mer peptide 1:1 | 0.1% |
| | OR | |
| | FITC insulin | |
| | OR | |
| | FITC-IgG | |
| | System A | Qs to 100 | d) Exemplary 12 mer peptide (mwt 1200), insulin (mwt 6000) and IgG (150,000) lipid vesicle formulation 4 (Peptide lipid vesicle formulation 4)

Preparation of System A (Oil in Water Sub-Micron Emulsion) for Formulations:

| Oil Phase | Labrafac CC | 5% |
|---|---|---|
| | Glyceryl monostearate NE | 1.2% |
| | Cetyl alcohol | 0.6% |
| | Synchrowax BB4 (beeswax) | 0.3% |
| | Propylparaben | 0.05% |
| Aqueous Phase | Arlasilk EFA (Phospholipid EFA) | 5% |
| | Methylparaben | 0.15% |
| | Milli-Q Water | Qs to 100 |

Preparation of Vesicles:

| Lipid Phase | Phospholipid (Sunlipon 90H) | 7% |
|---|---|---|
| | Cholesterol | 1.75% |
| | Oleth-2 | 1% |
| | Propylene glycol | 7% |
| Aqueous Phase | Rhodamine-12mer peptide:12mer peptide 1:1 | 0.1% |
| | OR | |
| | FITC insulin | |
| | OR | |
| | FITC-IgG | |
| | System A | Qs to 100 |

4) Nucleic acid lipid vesicle formulations

The following exemplary nucleic acid lipid vesicle lipid vesicles formulations were prepared using the process described above for exemplary ibuprofen formulation IB1.

a) Comparative plasmid lipid vesicle formulations F-TOM-1

Preparation of System A (Oil in Water Sub-Micron Emulsion) for F-TOM-1

| Oil Phase | Olive oil | 5% |
|---|---|---|
| | Glyceryl monostearate | 1.2% |
| | Cetyl alcohol | 0.6% |
| | Synchrowax BB4 (beeswax) | 0.3% |
| | Propyl paraben | 0.05% |
| Aqueous Phase | Phospholipid EFA | 5% |
| | Methylparaben | 0.1% |
| | Milli-Q Water | Qs to 100 |

Preparation of Vesicles:

| Lipid Phase | Phospholipon 90H | 10% |
|---|---|---|
| | Cholesterol | 2% |
| | Propylene glycol | 7% |
| Aqueous Phase | System A | Qs to 100 | b) Exemplary plasmid formulation lipid vesicle F-TOM-2

Preparation of System A (Oil in Water Sub-Micron Emulsion) for F-TOM-2

| Oil Phase | Olive oil | 5% |
|---|---|---|
| | Glyceryl monostearate | 1.2% |
| | Cetyl alcohol | 0.6% |
| | Synchrowax BB4 (beeswax) | 0.3% |
| | Propylparaben | 0.05% |
| Aqueous Phase | Gemini surfactant 16-3-16 | 0.1% |
| | Tween 80 | 0.5% |
| | Methylparaben | 0.1% |
| | Milli-Q Water | Qs to 100 |

Preparation of Vesicles:

| Lipid Phase | Phospholipon 90H | 10% |
|---|---|---|
| | Cholesterol | 2% |
| | Propylene glycol | 7% |
| Aqueous Phase | System A | Qs to 100 | c) Exemplary Plasmid Lipid Vesicle Formulation F-TOM-3

Preparation of System A (Oil in Water Sub-Micron Emulsion) for F-TOM-3

| Oil Phase | Labrafac CC (medium chain triglycerides) | 3% |
|---|---|---|
| | Phospholipid | 2% |
| Aqueous Phase | Gemini surfactant 12-3-12 | 0.1% |
| | Milli-Q Water | Qs to 100 |

Preparation of Vesicles:

| Lipid Phase | Phospholipon 90H | 10% |
|---|---|---|
| | Cholesterol | 2% |
| | Propylene glycol | 7% |
| Aqueous Phase | System A | Qs to 100 | d) Exemplary Plasmid Lipid Vesicle Formulation F-TOM-4
Preparation of System A (Oil in Water Sub-Micron Emulsion) for F-TOM-4

| Oil Phase | Labrafac CC (medium chain triglycerides) | 3% |
|---|---|---|
|  | Phospholipid | 2% |
| Aqueous Phase | Gemini surfactant12-7NCH3-12 | 0.1% |
|  | Milli-Q Water | Qs to 100 |

Preparation of Vesicles:

| Lipid Phase | Phospholipon 90H | 10% |
|---|---|---|
|  | Cholesterol | 2% |
|  | Propylene glycol | 7% |
| Aqueous Phase | System A | Qs to 100 | e) Exemplary Plasmid Lipid Vesicle Formulation F-TOM-5
Preparation of System A (Oil in Water Sub-Micron Emulsion) for F-TOM-5

| Oil Phase | Labrafac CC (medium chain triglycerides) | 3% |
|---|---|---|
|  | Phospholipid | 2% |
| Aqueous Phase | Gemini surfactant12-7NH-12 | 0.1% |
|  | Milli-Q Water | Qs to 100 |

Preparation of Vesicles:

| Lipid Phase | Phospholipon 90H | 10% |
|---|---|---|
|  | Lauroyl-capryloyl lysine methyl ester | 2.5% |
|  | Propylene glycol | 7% |
| Aqueous Phase | System A | Qs to 100 |

C. Results and Discussion

Cutaneous Delivery of Ibuprofen and Diclofenac

The results of the in vitro cell diffusion and skin homogenate assays (see Table 3 and Table 4 below) show the improvement of delivery of IB and DF was achieved by incorporating a penetration enhancer component into the exemplary biphasic lipid vesicle formulations. It was found that adding a hydrophobic non-ionic surfactant with an HLB<10, for example one with HLB 4-7 such as Oleth-2 enhanced delivery into the viable epidermis. Further enhancement could be achieved when an additional penetration enhancer such as a terpene (such as menthol, camphor, methylsalicylate) or alkaloid (such as piperine) was added (Table 3). The enhanced permeation effect of the hydrophobic non-ionic surfactant such as Oleth-2 could be further enhanced by increasing its concentration in the formulation (eg. from 1% to 2%) (Table 3).

TABLE 3

Cutaneous Delivery of Ibuprofen. The concentration of IB was measured in the skin homogenates using UPLC. Data presented as average ± s.d. (n = 4).(Whole skin = surface bound drug removed by two D-squame strips. Stripped skin = viable skin layers only; skin stripped 2 + 10 times with D-squame strips)

| Sample | Formulation type | Average amount of IB (mg/g skin) | Average amount of IB (mg/cm$^2$ skin) |
|---|---|---|---|
| IB0* whole skin | Biphasic vesicles | 0.29 ± 0.018 | 0.086 ± 0.009 |
| IB0* stripped skin | (comparative formula)* *same as F-TOM-1 | 0.30 ± 0.094 | 0.090 ± 0.05 |
| IB1 whole skin | Biphasic vesicles | 0.63 ± 0.108 | 0.12 ± 0.031 |
| IB1 stripped skin | + Oleth-2 (1%) | 0.54 ± 0.167 | 0.10 ± 0.049 |
| IB2 whole skin | Biphasic vesiclesIB1 | 0.97 ± 0.244 | 0.17 ± 0.063 |
| IB2 stripped skin | + Oleth-2 (1%) + Menthol + Camphor in System A | 0.94 ± 0.266 | 0.17 ± 0.062 |
| IB3A whole skin | Biphasic vesiclesIB1 | 0.928 ± 0.293 | 0.18 ± 0.078 |
| IB3A stripped skin | + Oleth-2 (1%) + piperine in lipid phase | 0.76 ± 0.437 | 0.15 ± 0.102 |
| IB3B whole skin | Biphasic vesiclesIB1 | 1.07 ± 0.126 | 0.20 ± 0.023 |
| IB3B stripped skin | + Oleth-2 (2%) + piperine | 0.72 ± 0.117 | 0.14 ± 0.043 |
| IB4A whole skin | Biphasic vesiclesIB1 | 1.02 ± 0.292 | 0.19 ± 0.062 |
| IB4A stripped skin | + Oleth-2 (1%) + methylsalicylate in lipid phase | 1.00 ± 00.385 | 0.19 ± 0.079 |
| IB4B whole skin | Biphasic vesiclesIB1 | 1.54 ± 0.498 | 0.27 ± 0.099 |
| IB4B stripped skin | + Oleth-2 (2%) + methylsalicylate in lipid phase | 1.23 ± 0.342 | 0.22 ± 0.070 |
| IB5A whole skin | Biphasic vesiclesIB1 | 0.67 ± 0.232 | 0.17 ± 0.081 |
| IB5A stripped skin | + Oleth-2 (1%) + nerol in lipid phase | 0.56 ± 0.322 | 0.14 ± 0.087 |
| IB5B whole skin | Biphasic vesiclesIB1 | 1.00 ± 0.656 | 0.19 ± 0.143 |
| IB5B stripped skin | + Oleth-2 (2%) + nerol in lipid phase | 0.71 ± 0.54 | 0.14 ± 0.118 |
| IB6A whole skin | Biphasic vesiclesIB1 | 0.41 ± 0.222 | 0.08 ± 0.055 |
| IB6A stripped skin | + Oleth-2 (1%) + thymol in lipid phase | 0.42 ± 00.114 | 0.08 ± 0.035 |

TABLE 3-continued

Cutaneous Delivery of Ibuprofen. The concentration of IB was measured in the skin homogenates using UPLC. Data presented as average ± s.d. (n = 4).(Whole skin = surface bound drug removed by two D-squame strips. Stripped skin = viable skin layers only; skin stripped 2 + 10 times with D-squame strips)

| Sample | Formulation type | Average amount of IB (mg/g skin) | Average amount of IB (mg/cm² skin) |
|---|---|---|---|
| IB6B whole skin | Biphasic vesiclesIB1 + Oleth-2 (2%) + thymol in lipid phase | 0.55 + 0.265 | 0.12 ± 0.051 |
| IB6B stripped skin | | 0.42 ± 0.131 | 0.094 ± 0.024 |

TABLE 4

Cutaneous Delivery of Diclofenac: The concentration of DF was measured in the skin homogenates using UPLC. Data presented as average ± s.d. (n = 4).(Whole skin = surface bound drug removed by two D-squame strips. Stripped skin = viable skin layers only; skin stripped 2 + 10 times with D-squame strips)

| Sample | Formulation type | Average amount if DF (mg/g skin) | Average amount of DF (mg/cm²) |
|---|---|---|---|
| DF1 whole skin | Biphasic vesicle + Piperine + Tween 80 + PEG-4 dilaurate in lipid phase | 0.72 ± 0.544 | 0.20 ± 0.191 |
| DF1 stripped skin | | 0.51 ± 0.372 | 0.13 ± 0.010 |
| DF2 whole skin | Biphasic vesicle + methylsalicylate + Tween 80 + PEG-4 dilaurate in lipid phase | 0.39 ± 0.258 | 0.11 ± 0.083 |
| DF2 stripped skin | | 0.72 ± 0.802* | 0.21 ± 0.247 |

*this data was relatively variable

Cutaneous Delivery of Peptide and Protein Therapeutic Agents

The cryosections of human skin samples treated in vitro in diffusion cells with topical formulations containing fluorescence labelled peptides and proteins were evaluated for the presence of fluorescent protein. The enhancement of delivery of protein and peptide compounds is shown with three compounds of increasing molecular weight (FIG. 1). It was shown that the incorporation of a penetration enhancer hydrophobic non-ionic surfactant with HLB<10 (eg. Oleth-2, sorbitan monopalmitate [Span 40], or PEG-4 dilaurate) increased the delivery of these proteins and peptides (FIG. 1). Table 5 indicates the relative fluorescence intensity of measured in the viable epidermal layers. While all of these hydrophobic non-ionic surfactants with HLB<10 were effective in delivery enhancement in the biphasic vesicles, the enhancement level was as follows (from highest to lowest): PEFA/Oleth-2>Tween 80/Span 40/Oleth-2>Tween 80/Span 40/PEG-4-dilaurate>PEFA/PEG-4-dilaurate. (The surfactant in italics is present in oil and water emulsion component of the comparative biphasic vesicles for the emulsification function; the surfactant in bold indicates the additional penetration enhancer for the penetration enhancer function).

TABLE 5

Average relative fluorescence intensity values obtained from the confocal microscopic images

| Formulation | Average relative fluorescence intensity in the viable epidermal layer |
|---|---|
| F1- TAMRA-13mer peptide (mwt 1440) | 24 |
| F2- TAMRA-13mer peptide (mwt 1440) | 40 |
| F3- TAMRA-13mer peptide (mwt 1200) | 50 |
| F4- TAMRA-13mer peptide (mwt 1440) | 212 |
| F1-FITC-insulin (mwt 6,000) | 10 |
| F2-FITC-insulin (mwt 6,000) | 40 |
| F3-FITC-insulin (mwt 6,000) | 15 |
| F4-FITC-insulin (mwt 6,000) | 20 |
| F1-FITC-IgG (mwt 150,000) | 15 |
| F2-FITC-IgG (mwt 150,000) | 20 |
| F3-FITC-IgG (mwt 150,000) | 40 |
| F4-FITC-IgG (mwt 150,000) | 50 |

Cutaneous Delivery of Nucleic Acids

Mouse skin samples treated with topical formulations containing plasmid DNA encoding the red tdTomato reporter gene were evaluated for the expression of tdTomato red fluorescent protein. Compared to the comparative biphasic vesicle (F-TOM-1 containing monocationic surfactant PEFA) the other formulations containing a replacement of PEFA, ie. dicationic gemini surfactants as complexing agents for the negatively charged plasmid DNA increased the delivery of plasmid DNA and the cutaneous gene expression in vivo in mice. All dicationic gemini surfactants used were effective in the delivery of plasmid DNA when incorporated into the biphasic vesicle structure. Enhancement was as follows (from highest to lowest): F-TOM-5 dicationic gemini surfactant 12-7NH-12/phospholipid emulsifier>F-TOM-4 dicationic gemini surfactant 12-7CH3-121 phospholipid emulsifier>F-TOM-3 dicationic gemini surfactant 12-3-12/phospholipid emulsifier>F-TOM-2* Tween 80/dicationic gemini surfactant 16-3-16 (surfactant in italics is an improved functional surfactant for biphasic vesicles to improve the encapsulation of highly negatively charged nucleic acids; surfactant in bold indicates the added HLB<10 synergistic penetration enhancer function) (Table 6). *F-TOM-2 is a variation for control formulation where the original biphasic vesicles prepared with Tween 80/PEFA were modified to Tween 80/gemini surfactant.

Figure 2:
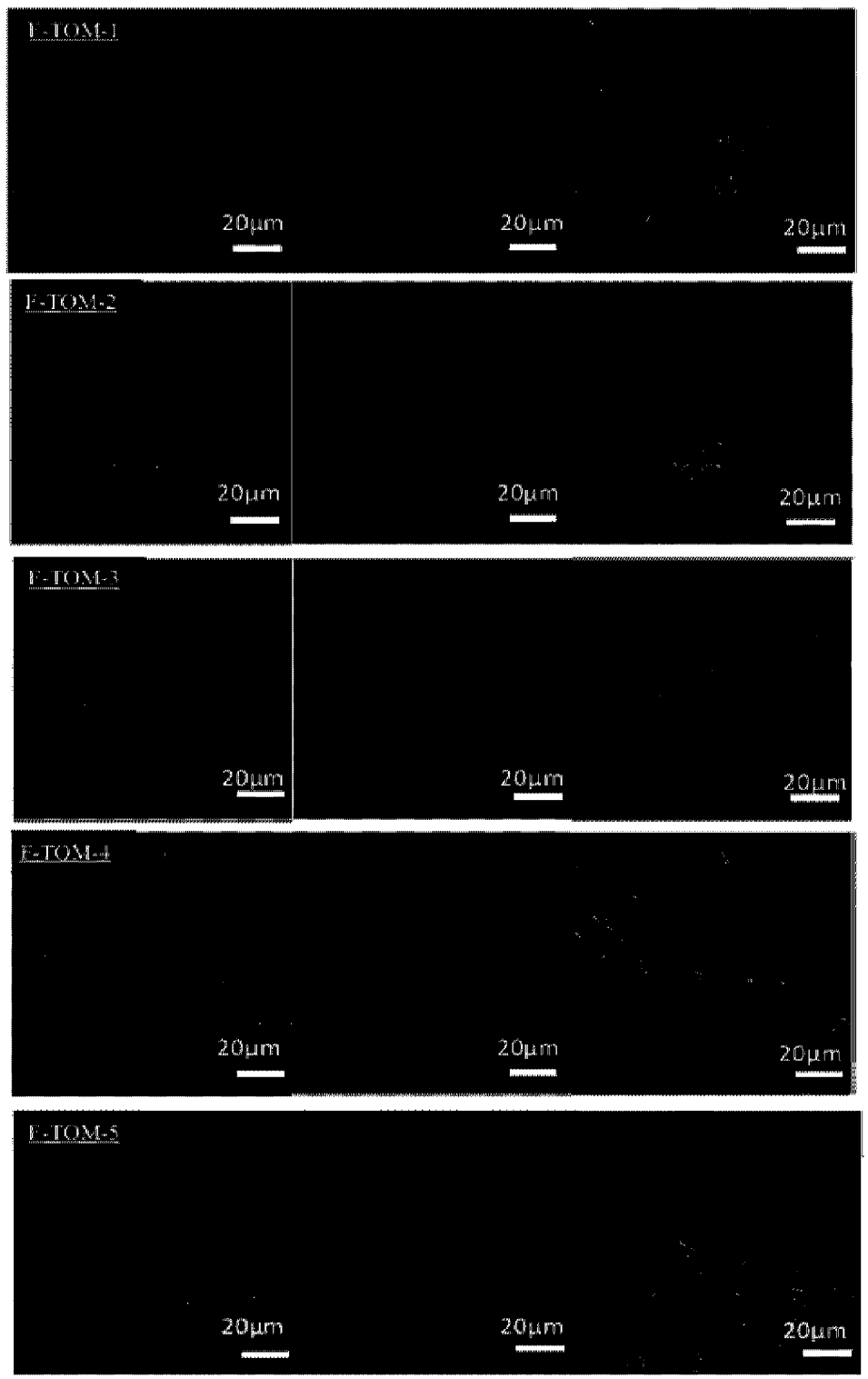
FIG. 2 shows confocal microscopic images of mouse skin treated with formulations nucleic acid lipid vesicle formulations F-TOM-1-5. For each formulation three panels are shown: the first panel: red channel for RFP expression (seen as light colored areas in the epidermis and dermis); second panel: general tissue stain (blue nuclear stain Syto 60); third panel: merged image).

All blank samples showed little to none background fluorescence (FIG. 2). Samples treated with intradermal naked pDNA show a significant amount of tdTomato expression (images not shown). For each formulation three panels are shown: the first panel: red channel for RFP expression (seen as light colored areas in the epidermis and dermis); second panel: general tissue stain (blue nuclear stain Syto 60); third panel: merged image).

TABLE 6

Average relative fluorescence intensity values obtained from the confocal microscopic images

| Formulation | Average relative fluorescence intensity in the viable epidermal layer (range) |
| --- | --- |
| F-TOM-1 (comparative biphasic vesicles) | 20-30 |
| F-TOM-2 | 50-100 |
| F-TOM-3 | 30-50 |
| F-TOM-4 | 50-100 |
| F-TOM-5 | 200-250 |

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

While certain embodiments have been illustrated and described, it should be understood that changes and modifications can be made therein in accordance with ordinary skill in the art without departing from the technology in its broader aspects as defined in the claims provided below.

The invention claimed is:

1. A biphasic lipid vesicle composition comprising:
   a) one or more lipid vesicles comprising a lipid bilayer comprising vesicle forming lipids,
   b) an oil-in-water emulsion entrapped in the biphasic lipid vesicles, wherein the oil-in-water emulsion comprises one or more components forming a non-covalent association with the lipid bilayer, wherein the oil-in-water emulsion comprises an aqueous continuous phase and a dispersed oil phase, and wherein the dispersed oil phase comprises droplets having an average diameter of less than 1 µm; and
   c) one or more penetration enhancing agents entrapped in the lipid bilayer or the oil-in-water emulsion;
   wherein the one or more penetration enhancing agents comprise one or more non-ionic surfactants having a hydrophilic-lipophilic balance (HLB) of about 10 or less comprising diethylene glycol monooleyl ether, sorbitan monopalmitate, or polyoxyethylene (4) dilaurate.

2. The composition of claim 1, wherein the one or more penetration enhancing agents are entrapped in the oil-in-water emulsion.

3. The composition of claim 1, wherein the one or more penetration enhancing agents are entrapped in the lipid bilayer and the oil-in-water emulsion.

4. The composition of claim 1, wherein the lipid bilayer comprises about 10 wt %, about 9 wt %, about 8 wt %, about 7 wt %, about 6 wt %, about 5 wt %, about 4 wt %, about 3 wt %, about 2 wt %, about 1 wt %, about 0.5 wt % or about 0.1 wt % of the one or more penetration enhancing agents.

5. The composition of claim 1, wherein the one or more penetration enhancing agents further comprise terpenes, alkaloids, salicylate derivatives, polycationic surfactants, or any combination thereof.

6. The composition of claim 5, wherein the terpenes comprise eugenol, d-limonene, menthol, menthone, farnesol, neridol, camphor, nerol, thymol, or any combination thereof.

7. The composition of claim 5, wherein the salicylate derivatives comprise ethyl salicylate, salicylic acid, acetylsalicylic acid, trolamine salicylate, or any combination thereof.

8. The composition of claim 5, wherein the alkaloids comprise piperine, lobeline, caffeine, theobromine theophylline, nicotine, colchicine, N-methyl pyrrolidone, hygrine, capsaicin, berberine, sanguinarine, histamine, pilocarpine, or any combination thereof.

9. The composition of claim 5, wherein the polycationic surfactants comprise one or more gemini cationic surfactants comprising a quaternary ammonium.

10. The composition of claim 5, wherein the polycationic surfactants comprise polycationic amino acids.

11. The composition of claim 1, wherein the oil-in-water emulsion of the biphasic lipid vesicles is stabilized by a second one or more surfactants comprising polyoxyethylene (10) cetyl ether and polysorbate 80.

12. The composition of claim 1, wherein the vesicle forming lipids comprise one or more of phospholipids, glycolipids, or ceramides.

13. The composition of claim 1, further comprising one or more compounds entrapped in the oil-in-water emulsion of the biphasic lipid vesicle, lipid bilayer of the biphasic lipid vesicle or both the oil-in-water emulsion and the lipid bilayer.

14. The composition of claim 13, wherein the one or more compounds comprise a small molecule with a weight of up to 1000 Daltons, protein, peptide, carbohydrate, nucleic acid, vaccine antigen, plant extract, or any combination thereof.

15. The composition of claim 1, wherein the biphasic lipid vesicle formulations further comprise one or more other lipid vesicle components comprising a fatty substance, penetration enhancer, surfactant, solvents, or any combination thereof.

16. The composition of claim 1, wherein the one or more non-ionic surfactant comprises an oleyl ether.

* * * * *